(12) United States Patent
Johnson et al.

(10) Patent No.: US 6,475,491 B1
(45) Date of Patent: *Nov. 5, 2002

(54) TREATMENT OF HIV AND OTHER VIRAL INFECTIONS USING COMBINATORIAL THERAPY

(75) Inventors: M. Ross Johnson, Chapel Hill; Dennis Michael Lambert, Cary, both of NC (US)

(73) Assignee: Trimeris, Inc., Durham, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,952

(22) PCT Filed: Jun. 6, 1996

(86) PCT No.: PCT/US96/09499

§ 371 (c)(1),
(2), (4) Date: May 29, 1998

(87) PCT Pub. No.: WO96/40191

PCT Pub. Date: Dec. 19, 1996

Related U.S. Application Data

(63) Continuation-in-part of application No. 08/481,957, filed on Jun. 7, 1995, now abandoned.

(51) Int. Cl.[7] .................................................. A61K 39/21
(52) U.S. Cl. .............................. 424/208.1; 424/184.1; 424/185.1; 424/204.1; 514/12; 514/45; 514/49; 514/50; 530/300; 530/324; 530/325
(58) Field of Search ........................... 424/184.1, 188.1, 424/204.1, 208.1; 514/12, 45, 49, 50; 530/300, 324, 325

(56) References Cited

U.S. PATENT DOCUMENTS

| | | | |
|---|---|---|---|
| 4,950,652 A | | 8/1990 | Carter |
| 5,077,280 A | | 12/1991 | Sommadossi et al. |
| 5,141,867 A | | 8/1992 | Ivanoff et al. |
| 5,393,883 A | | 2/1995 | Blumenhopf et al. |
| 5,464,933 A | * | 11/1995 | Bolognesi et al. ............ 530/324 |
| 5,656,480 A | * | 8/1997 | Wild et al. .................... 435/325 |

FOREIGN PATENT DOCUMENTS

| | | |
|---|---|---|
| WO | WO 90/07119 | 6/1990 |
| WO | WO 91/09872 | 7/1991 |
| WO | WO 92/22654 | 12/1992 |

OTHER PUBLICATIONS

Lambert, et al. : Synergistic drug interactions . . . : Antivir. Res.: 21 : pp. 327–342, 1993.*
Wild, et al.: Peptides corresponding to a prdictive . . . : P.N.A.C.: vol. 91: pp. 9770–9774, Oct. 1994.*
Fox: No Winners against HIV: Bio/Technology: vol. 12: p. 128, Feb. 1994.*
Najera et al., 1995, "*pol* Gene Quasispecies of Human Immunodeficiency Virus Mutations Associated with Drug Resistance in Virus from Patients Undergoing No Drug Therapy", J Virol 69:23–31.
Ho et al., 1995, "Rapid Turnover of Plasma Virions and CD4 Lymphocytes in HIV–1 Infection", Nature 373:123–126.
Wei et al., 1995, "Viral Dynamics in Human Immunodeficiency Virus Type 1 Infection", Nature 373:117–122.
Matthews et al., 1994, "Structural Rearrangements in the Transmembrane Glycoprotein After Receptor Binding", Immunol Rev 140:93–104.
Wild et al., 1994, "Peptides Corresponding to a Predicative α–Helical Domain of Human Immunodeficiency Virus Type 1 gp41 are Potent Inhibitors of Virus Infection", Proc Natl Acad Sci USA 91:9770–9774.
Lambert et al., 1993, "Synergistic Drug Interactions of an HIV–1 Protease Inhibitor with AZT in Different In Vitro Models of HIV–1 Infection", Antiviral Research 21:327–342.
Wild et al., 1992, "A Synthetic Peptide Inhibitor of Human Immunodeficiency Virus Replication: Correlation Between Solution Structure and Viral Inhibition", Proc Natl Acad Sci USA 89:10537–10541.
Mitsuya et al., 1990, "Molecular Targets for AIDS Therapy", Science 249:1533–1544.
Mitsuya et al., 1991, "Targeted Therapy of Human Immunodeficiency Virus–related Disease", FASEB J 5:2369–2381.
Schooley et al., 1990, "Recombinant Soluble CD4 Therapy in Patients with the Acquired Immunodeficiency Syndrome (AIDS) and AIDS–Related Complex", 1990, Ann Int Med 112:247–253.
Pritchard and Shipman, 1990, "A Three–dimensional Model to Analyze Drug–Drug Interactions", Antiviral Research 14:181–206.
Erickson et al., 1990, "Design, Activity, and 2.8 Å Crystal Structure of a $C_2$ Symmetric Inhibitor Complexed to HIV–1 Protease", Science 249:527–533.
Larder et al., 1989, "HIV with Reduced Sensitivity to Zidovudine (AZT) Isolated During Prolonged Therapy", Science 243:1731–1734.

(List continued on next page.)

*Primary Examiner*—James Housel
*Assistant Examiner*—Ulrike Winkler
(74) *Attorney, Agent, or Firm*—Pennie & Edmonds LLP; M. Bud Nelson

(57) ABSTRACT

Novel antiviral combinations for the treatment or prevention of viral infections, in particular, HIV, are disclosed. This new antiviral therapy employs either DP-178 or DP-107, viral fusion inhibitors, in combination with at least one other antiviral therapeutic agent. The combinations of the invention are better than single therapies alone, and in certain cases are synergistic. The use of DP-178 or DP-107 is an ideal therapy to combine with another antiviral, given both the novel mechanism which this therapeutic blocks HIV transmission and the non-toxicity of the therapeutic.

32 Claims, 20 Drawing Sheets

OTHER PUBLICATIONS

Figure 2:
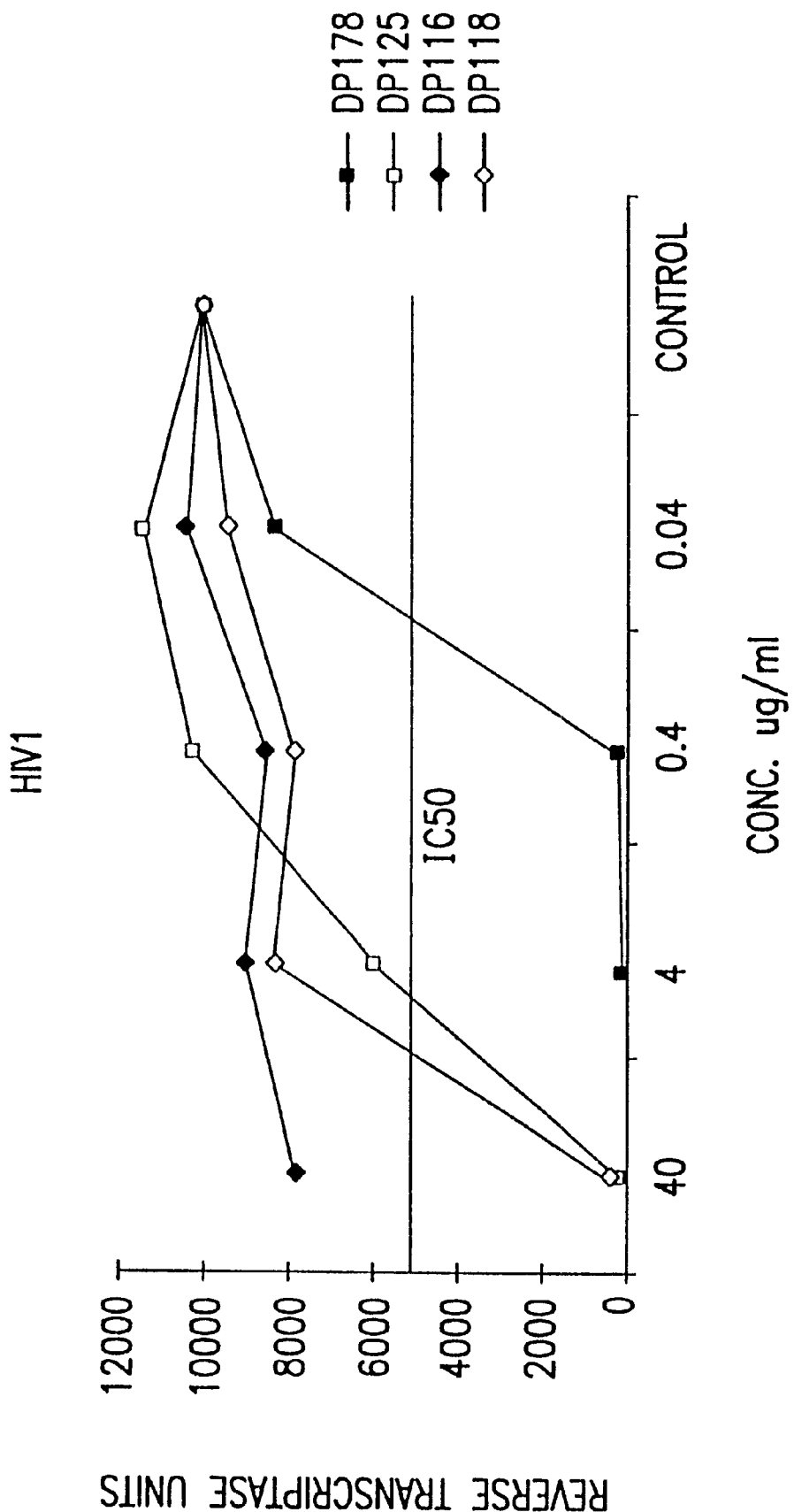

Hammerwskjold and Rekosh, 1989, "The Molecular Biology of the Human Immunodeficiency Virus", Biochem Biophys Acta 989:269–280.

Willey et al., 1988, "In Vitro Mutagenesis Identifies a Region Within the Envelope Gene of the Human Immunodeficiency Virus That Is Critical for Infectivity", J Virol 62:139–147.

Pottage et al., 1988, "Treatment of Human Immunodeficiency Virus–Related Thrombocytopenia With Zidovudine", JAMA 260:3045–3048.

Varmus, 1988, "Retroviruses", Science 240:1427–1439.

Smith et al., 1987, "Blocking of HIV–1 Infectivity by a Soluble, Secreted Form of the CD4 Antigen", Science 238:1704–1707.

Mitsuya and Broder, 1987, "Strategies for Antiviral Therapy in AIDS", Nature 325:773–778.

Matthews et al., 1987, "Interaction Between the Human T–cell Lymphotropic Virus Type $III_B$ Envelope Glycoprotein gp120 and the Surface Antigen CD4: Role of Carbohydrate in Binding and Cell Fusion", Proc Natl Acad Sci USA 84:5424–5428.

Fischl et al., 1987, "The Efficacy of Azidothymidine (AZT) In The Treatment of Patients with AIDS and AIDS–Related Complex", N Engl J Med 317:185–191.

McDougal et al., 1986, "Binding of HTLV–III/LAV to $T4^+T$ Cells by a Complex of the 110K Viral Protein and the T4 Molecule", Science 231:382–385.

Maddon et al., 1986, "The T4 Gene Encodes the AIDS Virus Receptor and Is Expressed in the Immune System and the Brain", Cell 47:333–348.

Pringle et al., 1985, "A Survey of Respiratory Syncytial Virus and Parainfluenza Virus Type 3 Neutralising and Immunoprecipitating Antibodies in Relation to Paget Disease", J Medical Virology 17:377–386.

Barin et al., 1985, "Virus Envelope Protein of HTLV–III Represents Major Target Antigen for Antibodies in AIDS Patients", Science 228:1094–1096.

Gallo et al., 1984, "Frequent Detection and Isolation of Cytopathic Retroviruses (HTLV–III) from Patients with AIDS and at Risk for AIDS", Science 224:500–503.

Chou and Talalay, 1984, "Quantitative Analysis of Dose–Effect Relationships: The Combined Effects of Multiple Drugs or Enzyme Inhibitors", Adv Enzyme Regul 22:27–55.

Dalgleish et al., 1984, "The CD4 (T4) Antigen is an Essential Component of the Receptor From the AIDS Retrovirus", Nature 312:763–768.

Barre–Sinossi et al., 1983, "Isolation of a T–Lymphotropic Retrovirus from a Patient at Risk for Acquired Immune Deficiency Syndrome (AIDS)", Science 220:868–871.

Goff et al., 1981, "Isolation and Properties of Moloney Murine Leukemia Virus Mutants: Use of a Rapid Assay for Release of Virion Reverse Transcriptase", J Virol 38:239–248.

* cited by examiner

| | |
|---|---|
| HIV1LAI (DP-178; SEQ ID:1) | YTSLIHSLIEESQNQQEKNEQELLELDKWASLWNWF |
| HIV1SF2 (DP-185; SEQ ID:3) | YTNTIYTLLEESQNQQEKNEQELLELDKWASLWNWF |
| HIV1RF (SEQ ID:4) | YTGIIYNLLEESQNQQEKNEQELLELDKWANLWNWF |
| HIV1MN (SEQ ID:5) | YTSLIYSLLEKSQIQQEKNEQELLELDKWASLWNWF |
| HIV2ROD (SEQ ID:6) | LEANISKSLEQAQIQQEKNMYELQKLNSWDIFGNWF |
| HIV2NIHZ (SEQ ID:7) | LEANISQSLEQAQIQQEKNMYELQKLNSWDVFTNWL |
| DP180 (SEQ ID:2) | SSESFTLLEQWNNWKLQLAEQWLEQINEKHYLEDIS |
| DP118 (SEQ ID:10) | QQLLDVVKRQQEMLRLTVWGTKNLQARVTAIEKYLKDQ |
| DP125 (SEQ ID:8) | CGGNNLLRAIEAQQHLLQLTVWGIKQLQARILAVERYLKDQ |
| DP116 (SEQ ID:9) | LQARILAVERYLKDQQQ |

FIG.5D (Table content rotated 90°, partial view)

| | | | | | | | | | | | | | |
|---|---|---|---|---|---|---|---|---|---|---|---|---|---|
| QN | QE | KNE | QE | LE | ED | K | | | | T622 | 230 | | |
| QN | QE | KNE | QE | LE | ED | KW | ASL | | | T623 | 3596 | | |
| QN | QE | KNE | QE | LE | ED | KW | ASL | WN | | T51 | >100000 | | |
| QN | QE | KNE | QE | LE | ED | KW | ASL | WN | | T641 | 98 | >100000 | |
| QN | QE | KNE | QE | LE | ED | KW | ASL | WN | | T640 | 15 | 7320 | |
| QN | QE | KNE | QE | LE | ED | | | | | T20 | 0.6 | | |
| 66 | 67 | 68 | 68 | 68 | 66 | | | | | | | | |
| 67 | 78 | 81 | 82 | 88 | 69 | | | | | | | | |
| 78 | 90 | 23 | 45 | 67 | 90 | WLIK | | | | | | | |
| 9 | | | | | 1 | | | | | | | | |
| WF | NIT | N | WL | LIK | IF | | 7 | | | | | | |
| | | | | | | | | | | T20 | 0.6 | >10000 | |
| WF | NIT | N | WL | LIK | IF | | | | | T639 | 21 | >10000 | |
| WF | NIT | N | WL | LIK | IF | | | | | T638 | 5 | >10000 | |
| WF | NIT | N | WL | LIK | IF | | | | | T637 | 12 | | |
| WF | NIT | N | WL | LIK | IF | | | | | T636 | 110 | | |
| WF | NIT | N | WL | LIK | IF | | | | | T635 | 139 | | |
| WF | NIT | N | WL | LIK | IF | | | | | T634 | 554 | | |
| WF | NIT | N | WL | LIK | IF | | | | | T633 | 186 | | |
| WF | NIT | N | WL | LIK | IF | | | | | T632 | 101800 | >10000 | |
| WF | NIT | N | WL | LIK | IF | | | | | T631 | >10000 | >10000 | |
| WF | NIT | N | WL | LIK | IF | | | | | T630 | >10000 | >10000 | |
| WF | NIT | N | WL | LIK | IF | | | | | T629 | >10000 | >10000 | |
| WF | NIT | N | WL | LIK | IF | | | | | T628 | >10000 | | |
| WF | NIT | N | WL | LIK | IF | | | | | T627 | >10000 | | |

\* CRUDE PREP RESULT

FIG. 5E

| | HIV-1/IIIB IC50(ng/ml) |
|---|---|
| T4 | >400000 |
| T228 | >50000 |
| T700 | >100000 |
| T715 | ND |
| T65/T716 | ND |
| T714 | ND |
| T712 | ND |
| T64 | ND |
| T63 | ND |
| T62 | ND |
| T3 | 3000 |
| T61/T102 | 64000 |
| T217 | 40000 |
| T218 | 25000 |
| T219 | 48000 |

| | |
|---|---|
| T220 | 59000 |
| T221 | 16000 |
| T234 | >100000 |
| T235 | 53000 |
| T570 | >100000 |
| T381 | 89000 |
| T382 | 190000 |
| T677 | 6310 |
| T376 | >100000 |
| T589 | 745000 |
| T377 | 69000 |
| T590 | 30290 |
| T378 | 95000 |
| T591 | 59000 |
| T270 | >200000 |
| T271 | 16000 |
| T272 | 1000 |
| T273 | >100000 |
| T608 | >100000 |
| T609 | >100000 |
| T610 | >100000 |
| T611 | 70000 |
| T612 | >100000 |
| T222 | 49000 |
| T223 | 57000 |
| T60/T224 | 77000 |
| T225 | >100000 |
| T226 | >100000 |
| T227 | >100000 |

FIG. 51

HIV-1 Bru 178 CONTRUCTS, MUTATIONS

| | | | AA# | | | | | | | | | | | | | |
|---|---|---|---|---|---|---|---|---|---|---|---|---|---|---|---|---|
| | Pt. MUTANTS | REMOVED | ADDED | 6 | 6 1/3 5 W | 6 3 3 Y | 6 4 4 T | 6 4 5 S | 6 4 6 L | 6 4 7 I | 6 4 8 H | 6 4 9 S | 6 5 0 L | 6 5 1 I | 6 5 2 E | 6 5 3 E | 6 5 4 S |
| T595 | | X | C13H27CO– | | | Y | T | S | L | I | H | S | L | I | E | E | S |
| T574 | | X | FREE TERMINI | | | Y | T | S | L | I | H | S | L | I | E | E | S |
| T680 | | X | NO AC– | | | Y | T | S | L | I | H | S | L | I | E | E | S |
| T573 | | X | DIG– | | | Y | T | S | L | I | H | S | L | I | E | E | S |
| T84 | | X | BIOTIN– | | | Y | T | S | L | I | H | S | L | I | E | E | S |
| T83 | | X | | | | | | | | | | | | | | | |
| T708 | | X | BIOTIN-NH(CH2)6CO– | | | Y | T | S | L | I | H | S | L | I | E | E | S |
| T707 | | X | BIOTIN-NH(CH2)4CO– | | | Y | T | S | L | I | H | S | L | I | E | E | S |
| T20 | | | | | | Y | T | S | L | I | H | S | L | I | E | E | S |
| T95 | X | | | | | | | | | | | | | | | | |
| T96 | X | | | | | Y | T | S | L | I | H | S | L | I | E | E | S |
| T97 | X | | | | | Y | T | S | L | I | H | S | L | I | E | E | S |
| T98 | X | | | | | Y | T | S | L | I | H | S | L | I | E | E | S |

| | | | | | | | | | | | | | | | | | | | | | | | | | | HIV-1/IIIB IC50 (ng/ml) |
|---|---|---|---|---|---|---|---|---|---|---|---|---|---|---|---|---|---|---|---|---|---|---|---|---|---|---|
| | | | | | | | | | | | | | 7 | | | | | 1 | | | | | 7 | | | |
| 5 | 5 | 5 | 5 | 6 | 6 | 6 | 6 | 6 | 6 | 6 | 6 | 6 | 6 | 6 | 6 | 6 | 6 | 6 | 6 | 6 | 7 | 7 | 7 | | | |
| 6 | 7 | 8 | 9 | 0 | 1 | 2 | 3 | 4 | 5 | 6 | 7 | 8 | 9 | 0 | 1 | 2 | 3 | 4 | 5 | 6 | 7 | 7 | 8 | | | |
| Q | N | Q | Q | E | K | N | E | Q | E | L | L | E | L | D | K | W | A | S | L | W | N | W | F | | | T595 | 112 |
| Q | N | Q | Q | E | K | N | E | Q | E | L | L | E | L | D | K | W | A | S | L | W | N | W | F | | | T574 | ND |
| Q | N | Q | Q | E | K | N | E | Q | E | L | L | E | L | D | K | W | A | S | L | W | N | W | F | | | T680 | 70 |
| Q | N | Q | Q | E | K | N | E | Q | E | L | L | E | L | D | K | W | A | S | L | W | N | W | F | | | T573 | ND |
| Q | N | Q | Q | E | K | N | E | Q | E | L | L | E | L | D | K | W | A | S | L | W | N | W | F | | | T84 | ND |
| Q | N | Q | Q | E | K | N | E | Q | E | L | L | E | L | D | K | W | A | S | L | W | N | W | F | | | T83 | 15 |
| Q | N | Q | Q | E | K | N | E | Q | E | L | L | E | L | D | K | W | A | S | L | W | N | W | F | | | T708 | ND |
| Q | N | Q | Q | E | K | N | E | Q | E | L | L | E | L | D | K | W | A | S | L | W | N | W | F | | | T707 | ND |
| Q | N | Q | Q | E | K | N | E | Q | E | L | L | E | L | D | K | W | A | S | L | W | N | W | F | | | T20 | 0.6 |
| Q | N | Q | Q | E | K | N | E | Q | E | L | L | E | L | D | K | W | A | S | L | A | N | W | F | | | T95 | 43 |
| Q | N | Q | Q | E | K | N | E | Q | E | L | L | E | L | D | K | W | A | S | L | A | N | W | F | | | T96 | 1 |
| Q | N | Q | Q | E | K | N | E | Q | E | L | L | E | L | D | K | W | A | S | L | W | N | W | F | | | T97 | 2 |
| Q | N | Q | Q | E | K | N | E | Q | E | L | L | E | L | D | K | W | A | S | L | W | N | W | F | | | T98 | 10 |

FIG. 5J

| | | | | | | | | | | | | | |
|---|---|---|---|---|---|---|---|---|---|---|---|---|---|
| T99 | X | | | | | | | Y | T | S | L | I | H | S | L | I | E | E | S |
| T103 | X | | | | | | | Y | T | S | L | I | Q | S | L | I | E | E | S |
| T212 | X | | | | | | | Y | T | S | L | I | H | S | L | I | E | E | S |
| T213 | X | | | | | | | Y | T | S | L | I | H | S | L | I | E | E | S |
| T214 | X | | | | | | | Y | T | S | L | I | H | S | L | I | E | Q | S |
| T215 | X | | | | | | | Y | T | S | L | I | H | S | L | I | E | E | S |
| T216 | X | | | | | | | Y | T | S | L | I | Q | S | L | I | E | Q | S |
| T229 | X | | | | | | | Y | T | S | L | I | Q | S | L | I | E | E | S |
| T230 | X | | | | | | | Y | T | S | L | I | H | S | L | I | E | E | S |
| T231 | X | | | | | | | Y | T | S | L | I | H | S | L | I | E | E | S |
| T379 | X | | | | | | | Y | T | S | L | I | H | S | L | I | E | E | S |
| T701 | X | | | | | | | Y | T | S | L | I | H | S | L | I | E | E | S |
| T702 | X | | | | | | | Y | T | S | L | I | H | S | L | I | E | E | S |
| T703 | X | | | | | | | Y | T | S | L | I | H | S | L | I | E | E | S |
| T704 | X | | | | | | | Y | T | S | L | I | H | S | L | I | E | E | S |
| T705 | X | | | | | | | Y | T | S | L | I | H | S | L | I | E | E | S |
| T706 | X | | | | | | | Y | T | S | L | I | H | S | L | I | E | E | S |
| T156 | X | | | | | | | L | L | D | N | F | E | S | T | W | E | Q | S |
| T89 | X | | | | | | | L | L | D | N | F | E | S | T | W | E | Q | S |
| T90 | X | | | | | | | L | S | N | L | L | Q | I | S | N | N | S | D |

FIG.5K

| | | | | | | | | | | | | |
|---|---|---|---|---|---|---|---|---|---|---|---|---|
| Q | N | Q | E | K | N | Q | E | L | L | D | K | W | A | S | L | W | N | F | T99 | 56 |
| Q | N | Q | E | K | N | Q | E | L | L | E | K | W | A | S | L | W | N | F | T103 | ND |
| Q | N | Q | E | K | N | Q | E | L | L | D | N | K | W | A | S | L | W | N | F | T212 | 3 |
| Q | N | Q | E | K | N | Q | E | L | L | D | K | W | A | S | L | W | N | F | T213 | 25 |
| Q | N | Q | E | K | N | Q | E | L | L | D | K | W | A | S | L | W | N | F | T214 | 19 |
| Q | N | Q | E | K | N | Q | E | L | L | D | K | W | A | S | L | W | N | F | T215 | 23 |
| Q | N | Q | E | K | N | Q | Q | L | L | Q | K | W | A | S | L | W | N | F | T216 | 1000 |
| Q | N | Q | E | K | N | Q | E | L | L | E | K | W | A | S | L | A | N | A | T229 | >100000 |
| Q | N | Q | E | K | N | Q | E | L | L | D | K | W | A | S | L | W | N | F | T230 | 6 |
| Q | N | Q | E | K | N | Q | E | L | L | D | K | E | A | S | L | W | N | F | T231 | 4 |
| Q | N | Q | E | K | N | Q | E | L | L | F | D | K | W | A | S | L | F | N | F | T379 | 0.3 |
| Q | N | Q | E | K | N | Q | E | L | L | D | K | W | A | S | L | W | N | F | T701 | 3 |
| Q | N | Q | E | K | L | Q | E | L | L | D | K | W | A | S | P | W | N | F | T702 | 36 |
| Q | N | Q | E | K | N | Q | E | L | L | D | K | W | A | S | L | W | N | F | T703 | 0.5 |
| Q | N | Q | E | K | N | Q | E | L | L | D | K | P | A | S | L | W | N | F | T704 | 510 |
| Q | N | Q | E | K | N | Q | E | L | L | D | K | W | A | S | L | W | N | F | T705 | 14 |
| Q | N | Q | E | K | N | Q | E | L | L | D | K | W | A | L | Q | E | Y | W | N | S | F | T706 | 68 |
| K | E | L | W | E | Q | Q | E | I | S | I | Q | N | L | H | K | S | A | L | Q | E | Y | W | N | T156 | 80000 |
| K | E | L | W | E | Q | Q | E | I | S | I | Q | N | L | H | K | S | A | L | Q | E | Y | W | N | T89 | >100000 |
| E | W | L | E | A | L | E | I | E | H | E | K | W | K | L | T | Q | W | Q | S | Y | E | Q | F | T90 | >100000 |

FIG.5L

FIG. 6A

HIV-1 BRU DP-107 PEPTIDES

| | TRUNCATION | ADDITION | | | | M | T | L | T | V | Q | A | R | Q | L | L | S | Q | I | V | Q | Q | Q | N | N | L | L | R | A | I | E | A | Q | Q | H | L | L | L | Q | L | T | V | W | G | I | K | Q | L |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | V | | | | | | | | | | | | | | | | | | | | | | | | | | | | | | | | | | | | | | | | | | | |
| T10 | 28-MER | UNBLOCKED | | | | M | T | L | T | V | Q | A | R | Q | L | L | S | Q | I | V | Q | Q | Q | N | N | L | L | R | A | I | E | A | Q | Q | H | L | L | L | Q | L | T | | | | | | | |
| T37 | 28-MER | | | | | | M | T | L | T | V | Q | A | R | Q | L | L | S | Q | I | V | Q | Q | Q | N | N | L | L | R | A | I | E | A | Q | Q | H | L | L | L | Q | L | T | V | | | | | |
| T48 | 28-MER | | | | | | | M | T | L | T | V | Q | A | R | Q | L | L | S | Q | I | V | Q | Q | Q | N | N | L | L | R | A | I | E | A | Q | Q | H | L | L | L | Q | L | T | | | | | |
| T36 | 28-MER | | | | | | | | | | | Q | A | R | Q | L | L | S | Q | I | V | Q | Q | Q | N | N | L | L | R | A | I | E | A | Q | Q | H | L | L | L | Q | L | T | | | | | |
| T8 | 28-MER | UNBLOCKED | | | | | | | | | | | R | Q | L | L | S | Q | I | V | Q | Q | Q | N | N | L | L | R | A | I | E | A | Q | Q | H | L | L | L | Q | L | T | V | W | G | I | K | Q | L |
| T33 | 28-MER | | | | | | | | | | | | | | | | | | | | V | Q | Q | Q | N | N | L | L | R | A | I | E | A | Q | Q | H | L | L | L | Q | L | T | V | W | G | I | K | Q | L |
| T21 | 38-MER | | | | | | | | | | | | | | | | | | | | V | Q | Q | Q | N | N | L | L | R | A | I | E | A | Q | Q | H | L | L | L | Q | L | T | V | W | G | I | K | Q | L |
| T85 | | BIOTIN | | | | | | | | | | | | | | | | | | | | | | BIOTIN | N | N | L | L | R | A | I | E | A | Q | Q | H | L | L | L | Q | L | T | V | W | G | I | K | Q | L |
| T1 | | X | | | | | | | | | | | | | | | | | | | | | | | | N | N | L | L | R | A | I | E | A | Q | Q | H | L | L | L | Q | L | T | V | W | G | I | K | Q | L |
| T2 | | X | UNBLOCKED | | | | | | | | | | | | | | | | | | | | | | | | | | | | | | | | | | | | | | | | | | | | G | I | K | Q | L |
| T7 | | X | UNBLOCKED | | | | | | | | | | | | | | | | | | | | | | | | | | | | | | | | | | | | | | | | | | | | | | | |
| T34 | | X | | | | | | | | | | | | | | | | | | | | | | | | | | | | | | | | | | | | | | | | | | | | | | | | |
| T6 | 28-MER | UNBLOCKED | | | | | | | | | | | | | | | | | | | | | | | | | | | | | | | A | Q | Q | H | L | L | L | Q | L | T | V | W | G | I | K | Q | L |
| T35 | 28-MER | | | | | | | | | | | | | | | | | | | | | | | | | | | | | | | | | Q | H | L | L | L | Q | L | T | V | W | G | I | K | Q | L |
| T5 | 28-MER | | | | | | | | | | | | | | | | | | | | | | | | | | | | | | | | | | | | | | | | | V | W | G | I | K | Q | L |

| | | | | | | | | | | | | | | | | | | | | | | |
|---|---|---|---|---|---|---|---|---|---|---|---|---|---|---|---|---|---|---|---|---|---|---|
| | | | | | | | | | | | | | | | | | | | | 6 | | |
| | | | | | | | | | | | | | | | | | | | | 0 | | |
| | | | | | | | | | | | | | | | | | | | | 2 | | |
| Q | A | R | I | L | A | V | E | R | Y | L | K | D | Q | Q | L | L | G | I | W | G | | |
| | | | | | | | | | | | | | | | | | | | | | | HIV/IIIB IC50(μg/ml) |
| | | | | | | | | | | | | | | | | | | | | | T10 | 50 |
| | | | | | | | | | | | | | | | | | | | | | T37 | 75* |
| | | | | | | | | | | | | | | | | | | | | | T48 | 83* |
| | | | | | | | | | | | | | | | | | | | | | T36 | 45* |
| | | | | | | | | | | | | | | | | | | | | | T8 | 50 |
| | | | | | | | | | | | | | | | | | | | | | T33 | >100* |
| Q | A | R | I | L | A | V | E | R | Y | L | K | D | Q | | | | | | | | T21 | 2 |
| Q | A | R | I | L | A | V | E | R | Y | L | K | D | Q | | | | | | | | T86 | 2 |
| Q | A | R | I | L | A | V | E | R | Y | L | K | D | Q | | | | | | | | T1 | >100 |
| | | | | | | | | | | | | | | | | | | | | | T2 | ND |
| Q | A | R | I | L | A | V | | | | | | | | | | | | | | | T7 | 26 |
| A | R | I | L | A | V | | | | | | | | | | | | | | | | T34 | >100* |
| Q | A | R | I | L | A | V | E | R | Y | L | K | D | Q | | | | | | | | T6 | 44 |
| Q | A | R | I | L | A | V | E | R | Y | L | K | D | Q | | | | | | | | T35 | >100* |
| Q | A | R | I | L | A | V | E | R | Y | L | K | D | Q | Q | L | L | G | I | W | G | T3 | 55 |

FIG.6B

| SIMIAN IMMUNODEFICIENCY VIRUS MM251 | | |
|---|---|---|
| DP178-LIKE | | |
| RESIDUE | 245 | TWQEWERKVDFLEENITALLEEAQIQQEKNMYELQKLNSWDVFGNWF |
| T- 390 | 245 | TWQEWERKVDFLEENITALLEEAQIQQEKNMYELQ |
| T- 391 | 246 | WQEWERKVDFLEENITALLEEAQIQQEKNMYELQK |
| T- 392 | 247 | QEWERKVDFLEENITALLEEAQIQQEKNMYELQKL |
| T- 393 | 248 | EWERKVDFLEENITALLEEAQIQQEKNMYELQKLN |
| T- 394 | 249 | WERKVDFLEENITALLEEAQIQQEKNMYELQKLNS |
| T- 395 | 250 | ERKVDFLEENITALLEEAQIQQEKNMYELQKLNSW |
| T- 396 | 251 | RKVDFLEENITALLEEAQIQQEKNMYELQKLNSWD |
| T- 397 | 252 | KVDFLEENITALLEEAQIQQEKNMYELQKLNSWDV |
| T- 398 | 253 | VDFLEENITALLEEAQIQQEKNMYELQKLNSWDVF |
| T- 399 | 254 | DFLEENITALLEEAQIQQEKNMYELQKLNSWDVFG |
| T- 400 | 255 | FLEENITALLEEAQIQQEKNMYELQKLNSWDVFGN |

FIG.7A

| 291 | RESIDUE | 47 | | ANTIVIRAL ACTIVITY SIV | | | | | | | |
|---|---|---|---|---|---|---|---|---|---|---|---|
| 280 | | 35 | | T390 | | | | | | | NT |
| 281 | | 35 | | T391 | | | | | | | +++ |
| 282 | | 35 | | T392 | | | | | | | +++ |
| 283 | | 35 | | T393 | | | | |

```
                        SEQUENCE LISTING

<160> NUMBER OF SEQ ID NOS: 82

<210> SEQ ID NO 1
<211> LENGTH: 36
<212> TYPE: PRT
<213> ORGANISM: Human immunodeficiency virus

<400> SEQUENCE: 1

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 36
<212> TYPE: PRT
<213> ORGANISM: Human immunodeficiency virus

<400> SEQUENCE: 2

Ser Ser Glu Ser Phe Thr Leu Leu Glu Gln Trp Asn Asn Trp Lys Leu
 1               5                  10                  15

Gln Leu Ala Glu Gln Trp Leu Glu Gln Ile Asn Glu Lys His Tyr Leu
            20                  25                  30

Glu Asp Ile Ser
        35

<210> SEQ ID NO 3
<211> LENGTH: 36
<212> TYPE: PRT
<213> ORGANISM: Human immunodeficiency virus

<400> SEQUENCE: 3

Tyr Thr Asn Thr Ile Tyr Thr Leu Leu Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 4
<211> LENGTH: 36
<212> TYPE: PRT
<213> ORGANISM: Human immunodeficiency virus

<400> SEQUENCE: 4

Tyr Thr Gly Ile Ile Tyr Asn Leu Leu Glu Glu Ser Gln Asn Gln Gln
 1               5                  10                  15

Glu Lys Asn Glu Gln Glu Leu Leu Glu Leu Asp Lys Trp Ala Asn Leu
            20                  25                  30

Trp Asn Trp Phe
```

<210> SEQ ID NO 5
<211> LENGTH: 36
<212> TYPE: PRT
<213> ORGANISM: Human immunodeficiency virus

<400> SEQUENCE: 5

Tyr Thr Ser Leu Ile Tyr Ser Leu Leu Glu Lys Ser Gln Thr Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 6
<211> LENGTH: 36
<212> TYPE: PRT
<213> ORGANISM: Human immunodeficiency virus

<400> SEQUENCE: 6

Leu Glu Ala Asn Ile Ser Lys Ser Leu Glu Gln Ala Gln Ile Gln Gln
1               5                   10                  15

Glu Lys Asn Met Tyr Glu Leu Gln Lys Leu Asn Ser Trp Asp Ile Phe
            20                  25                  30

Gly Asn Trp Phe
        35

<210> SEQ ID NO 7
<211> LENGTH: 36
<212> TYPE: PRT
<213> ORGANISM: Human immunodeficiency virus

<400> SEQUENCE: 7

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 8
<211> LENGTH: 41
<212> TYPE: PRT
<213> ORGANISM: Human immunodeficiency virus

<400> SEQUENCE: 8

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 9
<211> LENGTH: 17
<212> TYPE: PRT
<213> ORGANISM: Human immunodeficiency virus

<400> SEQUENCE: 9

Leu Gln Ala Arg Ile Leu Ala Val Glu Arg Tyr Leu Lys Asp Gln Gln

Gln

<210> SEQ ID NO 10
<211> LENGTH: 38
<212> TYPE: PRT
<213> ORGANISM: Human immunodeficiency virus

<400> SEQUENCE: 10

Gln Gln Leu Leu Asp Val Val Lys Arg Gln Gln Glu Met Leu Arg Leu
 1               5                  10                  15

Thr Val Trp Gly Thr Lys Asn Leu Gln Ala Arg Val Thr Ala Ile Glu
            20                  25                  30

Lys Tyr Leu Lys Asp Gln
        35

<210> SEQ ID NO 11
<211> LENGTH: 58
<212> TYPE: PRT
<213> ORGANISM: Human immunodeficiency virus

<400> SEQUENCE: 11

Asn Lys Ser Leu Glu Gln Ile Trp Asn Asn Met Thr Trp Met Glu Trp
 1               5                  10                  15

Asp Arg Glu Ile Asn Asn Tyr Thr Ser Leu Ile His Ser Leu Ile Glu
            20                  25                  30

Glu Ser Gln Asn Gln Gln Glu Lys Asn Glu Gln Glu Leu Leu Glu Leu
        35                  40                  45

Asp Lys Trp Ala Ser Leu Trp Asn Trp Phe
        50                  55

<210> SEQ ID NO 12
<211> LENGTH: 35
<212> TYPE: PRT
<213> ORGANISM: Human immunodeficiency virus

<400> SEQUENCE: 12

Trp Met Glu Trp Asp Arg Glu Ile Asn Asn Tyr Thr Ser Leu Ile Gly
 1               5                  10                  15

Ser Leu Ile Glu Glu Ser Gln Asn Gln Gln Glu Lys Asn Glu Gln Glu
            20                  25                  30

Leu Leu Glu
        35

<210> SEQ ID NO 13
<211> LENGTH: 49
<212> TYPE: PRT
<213> ORGANISM: Human immunodeficiency virus

<400> SEQUENCE: 13

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe Asn Ile Thr Asn Trp Leu Trp Leu Ile Lys Ile Phe
        35                  40                  45

Ile

<210> SEQ ID NO 14

```
<211> LENGTH: 28
<212> TYPE: PRT
<213> ORGANISM: Human immunodeficiency virus

<400> SEQUENCE: 14

Glu Ala Ala Arg Glu Ala Ala Arg Glu Ala Ala Arg Leu
 1               5                  10                  15

Glu Leu Asp Lys Trp Ala Ser Leu Trp Asn Trp Phe
            20                  25

<210> SEQ ID NO 15
<211> LENGTH: 28
<212> TYPE: PRT
<213> ORGANISM: Human immunodeficiency virus

<400> SEQUENCE: 15

Arg Met Lys Gln Leu Glu Asp Lys Val Glu Glu Leu Leu Ser Lys Leu
 1               5                  10                  15

Glu Leu Asp Lys Trp Ala Ser Leu Trp Asn Trp Phe
            20                  25

<210> SEQ ID NO 16
<211> LENGTH: 28
<212> TYPE: PRT
<213> ORGANISM: Human immunodeficiency virus

<400> SEQUENCE: 16

Phe Trp Asn Trp Leu Ser Ala Trp Lys Asp Leu Glu Leu Lys Ser Leu
 1               5                  10                  15

Leu Glu Glu Val Lys Asp Glu Leu Gln Lys Met Arg
            20                  25

<210> SEQ ID NO 17
<211> LENGTH: 35
<212> TYPE: PRT
<213> ORGANISM: Human immunodeficiency virus

<400> SEQUENCE: 17

Arg Met Lys Gln Leu Glu Asp Lys Val Glu Glu Leu Leu Ser Lys Asn
 1               5                  10                  15

Tyr His Leu Glu Asn Glu Leu Glu Leu Asp Lys Trp Ala Ser Leu Trp
            20                  25                  30

Asn Trp Phe
        35

<210> SEQ ID NO 18
<211> LENGTH: 30
<212> TYPE: PRT
<213> ORGANISM: Human immunodeficiency virus

<400> SEQUENCE: 18

Phe Trp Asn Trp Leu Ser Ala Trp Lys Asp Leu Glu Leu Tyr Pro Gly
 1               5                  10                  15

Ser Leu Glu Leu Asp Lys Trp Ala Ser Leu Trp Asn Trp Phe
            20                  25                  30

<210> SEQ ID NO 19
<211> LENGTH: 15
<212> TYPE: PRT
<213> ORGANISM: Human immunodeficiency virus

<400> SEQUENCE: 19
```

Cys Leu Glu Leu Asp Lys Trp Ala Ser Leu Trp Asn Trp Phe Cys
1               5                   10                  15

<210> SEQ ID NO 20
<211> LENGTH: 15
<212> TYPE: PRT
<213> ORGANISM: Human immunodeficiency virus

<400> SEQUENCE: 20

Cys Leu Glu Leu Asp Lys Trp Ala Ser Leu Ala Asn Trp Phe Cys
1               5                   10                  15

<210> SEQ ID NO 21
<211> LENGTH: 15
<212> TYPE: PRT
<213> ORGANISM: Human immunodeficiency virus

<400> SEQUENCE: 21

Cys Leu Glu Leu Asp Lys Trp Ala Ser Leu Trp Asn Phe Phe Cys
1               5                   10                  15

<210> SEQ ID NO 22
<211> LENGTH: 13
<212> TYPE: PRT
<213> ORGANISM: Human immunodeficiency virus

<400> SEQUENCE: 22

Leu Glu Leu Asp Lys Trp Ala Ser Leu Ala Asn Ala Phe
1               5                   10

<210> SEQ ID NO 23
<211> LENGTH: 13
<212> TYPE: PRT
<213> ORGANISM: Human immunodeficiency virus

<400> SEQUENCE: 23

Leu Glu Leu Asp Lys Trp Ala Ser Leu Phe Asn Phe Phe
1               5                   10

<210> SEQ ID NO 24
<211> LENGTH: 13
<212> TYPE: PRT
<213> ORGANISM: Human immunodeficiency virus

<400> SEQUENCE: 24

Leu Glu Leu Asp Lys Trp Ala Ser Leu Trp Asn Ala Phe
1               5                   10

<210> SEQ ID NO 25
<211> LENGTH: 13
<212> TYPE: PRT
<213> ORGANISM: Human immunodeficiency virus

<400> SEQUENCE: 25

Leu Glu Leu Asp Lys Trp Ala Ser Leu Trp Asn Trp Ala
1               5                   10

<210> SEQ ID NO 26
<211> LENGTH: 13
<212> TYPE: PRT
<213> ORGANISM: Human immunodeficiency virus

<400> SEQUENCE: 26

Leu Glu Leu Asp Lys Trp Ala Ser Ala Trp Asn Trp Phe
1               5                   10

<210> SEQ ID NO 27
<211> LENGTH: 13
<212> TYPE: PRT
<213> ORGANISM: Human immunodeficiency virus

<400> SEQUENCE: 27

Leu Glu Leu Asp Lys Ala Ala Ser Leu Trp Asn Trp Phe
 1               5                  10

<210> SEQ ID NO 28
<211> LENGTH: 13
<212> TYPE: PRT
<213> ORGANISM: Human immunodeficiency virus

<400> SEQUENCE: 28

Leu Lys Leu Asp Lys Trp Ala Ser Leu Trp Asn Trp Phe
 1               5                  10

<210> SEQ ID NO 29
<211> LENGTH: 13
<212> TYPE: PRT
<213> ORGANISM: Human immunodeficiency virus

<400> SEQUENCE: 29

Leu Glu Leu Lys Lys Trp Ala Ser Leu Trp Asn Trp Phe
 1               5                  10

<210> SEQ ID NO 30
<211> LENGTH: 39
<212> TYPE: PRT
<213> ORGANISM: Human immunodeficiency virus

<400> SEQUENCE: 30

Cys Gly Gly Tyr Thr Ser Leu Ile His Ser Leu Ile Glu Glu Ser Gln
 1               5                  10                  15

Asn Gln Gln Glu Lys Asn Glu Gln Glu Leu Leu Glu Leu Asp Lys Trp
            20                  25                  30

Ala Ser Leu Trp Asn Trp Phe
        35

<210> SEQ ID NO 31
<211> LENGTH: 36
<212> TYPE: PRT
<213> ORGANISM: Human immunodeficiency virus

<400> SEQUENCE: 31

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Ala Phe
        35

<210> SEQ ID NO 32
<211> LENGTH: 36
<212> TYPE: PRT
<213> ORGANISM: Human immunodeficiency virus

<400> SEQUENCE: 32

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Ala Asn Trp Phe
        35

<210> SEQ ID NO 33
<211> LENGTH: 36
<212> TYPE: PRT
<213> ORGANISM: Human immunodeficiency virus

<400> SEQUENCE: 33

Tyr Thr Ser Leu Ile His Ser Leu Ile Glu Glu Ser Gln Asn Gln Gln
 1               5                  10                  15

Glu Lys Asn Glu Gln Gln Leu Leu Glu Leu Asp Lys Trp Ala Ser Leu
            20                  25                  30

Trp Asn Trp Phe
        35

<210> SEQ ID NO 34
<211> LENGTH: 36
<212> TYPE: PRT
<213> ORGANISM: Human immunodeficiency virus

<400> SEQUENCE: 34

Tyr Thr Ser Leu Ile His Ser Leu Ile Glu Glu Ser Gln Asn Gln Gln
 1               5                  10                  15

Glu Lys Asn Glu Gln Glu Leu Leu Gln Leu Asp Lys Trp Ala Ser Leu
            20                  25                  30

Trp Asn Trp Phe
        35

<210> SEQ ID NO 35
<211> LENGTH: 36
<212> TYPE: PRT
<213> ORGANISM: Human immunodeficiency virus

<400> SEQUENCE: 35

Tyr Thr Ser Leu Ile His Ser Leu Ile Glu Glu Ser Gln Asn Gln Gln
 1               5                  10                  15

Glu Lys Asn Gln Gln Glu Leu Leu Gln Leu Asp Lys Trp Ala Ser Leu
            20                  25                  30

Trp Asn Trp Phe
        35

<210> SEQ ID NO 36
<211> LENGTH: 36
<212> TYPE: PRT
<213> ORGANISM: Human immunodeficiency virus

<400> SEQUENCE: 36

Tyr Thr Ser Leu Ile Gln Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 37
<211> LENGTH: 36
<212> TYPE: PRT
<213> ORGANISM: Human immunodeficiency virus

<400> SEQUENCE: 37

Tyr Thr Ser Leu Ile His Ser Leu Ile Glu Glu Ser Gln Gln Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 38
<211> LENGTH: 36
<212> TYPE: PRT
<213> ORGANISM: Human immunodeficiency virus

<400> SEQUENCE: 38

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asn Lys Trp Ala Ser Leu
            20                  25                  30

Trp Asn Trp Phe
        35

<210> SEQ ID NO 39
<211> LENGTH: 36
<212> TYPE: PRT
<213> ORGANISM: Human immunodeficiency virus

<400> SEQUENCE: 39

Tyr Thr Ser Leu Ile His Ser Leu Ile Glu Gln Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 40
<211> LENGTH: 36
<212> TYPE: PRT
<213> ORGANISM: Human immunodeficiency virus

<400> SEQUENCE: 40

Tyr Thr Ser Leu Ile His Ser Leu Ile Gln Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 41
<211> LENGTH: 36
<212> TYPE: PRT
<213> ORGANISM: Human immunodeficiency virus

<400> SEQUENCE: 41

Tyr Thr Ser Leu Ile His Ser Leu Ile Gln Gln Ser Gln Asn Gln Gln
1               5                   10                  15

Gln Lys Asn Gln Gln Gln Leu Leu Gln Leu Asp Lys Trp Ala Ser Leu
            20                  25                  30

Trp Asn Trp Phe
        35

<210> SEQ ID NO 42
<211> LENGTH: 36
<212> TYPE: PRT
<213> ORGANISM: Human immunodeficiency virus

<400> SEQUENCE: 42

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Ala Asn Ala Ala
        35

<210> SEQ ID NO 43
<211> LENGTH: 36
<212> TYPE: PRT
<213> ORGANISM: Human immunodeficiency virus

<400> SEQUENCE: 43

Tyr Thr Ser Leu Ile His Ser Leu Ile Glu Glu Ser Gln Asn Gln Gln
1               5                   10                  15

Glu Lys Asn Glu Gln Gln Leu Leu Glu Leu Asp Lys Trp Ala Ser Leu
            20                  25                  30

Trp Asn Trp Phe
        35

<210> SEQ ID NO 44
<211> LENGTH: 36
<212> TYPE: PRT
<213> ORGANISM: Human immunodeficiency virus

<400> SEQUENCE: 44

Tyr Thr Ser Leu Ile Gln Ser Leu Ile Glu Glu Ser Gln Asn Gln Gln
1               5                   10                  15

Glu Lys Asn Glu Gln Gln Leu Leu Glu Leu Asp Lys Trp Ala Ser Leu
            20                  25                  30

Trp Asn Trp Phe
        35

<210> SEQ ID NO 45
<211> LENGTH: 36
<212> TYPE: PRT
<213> ORGANISM: Human immunodeficiency virus

<400> SEQUENCE: 45

Tyr Thr Ser Leu Ile His Ser Leu Ile Glu Glu Ser Gln Asn Gln Gln
1               5                   10                  15

Glu Lys Asn Glu Gln Gly Leu Leu Glu Leu Asp Lys Trp Ala Ser Leu
            20                  25                  30

Phe Asn Phe Phe
        35

<210> SEQ ID NO 46
<211> LENGTH: 36
<212> TYPE: PRT
<213> ORGANISM: Human immunodeficiency virus

<400> SEQUENCE: 46

Tyr Thr Ser Leu Ile His Ser Leu Ile Glu Glu Ser Gln Asn Leu Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 47
<211> LENGTH: 36
<212> TYPE: PRT
<213> ORGANISM: Human immunodeficiency virus

<400> SEQUENCE: 47

Tyr Thr Ser Leu Ile His Ser Leu Ile Glu Glu Ser Gln Asn Gln Gln
 1               5                  10                  15

Glu Lys Leu Glu Gln Glu Leu Leu Glu Leu Asp Lys Trp Ala Ser Leu
            20                  25                  30

Trp Asn Trp Phe
        35

<210> SEQ ID NO 48
<211> LENGTH: 36
<212> TYPE: PRT
<213> ORGANISM: Human immunodeficiency virus

<400> SEQUENCE: 48

Tyr Thr Ser Leu Ile His Ser Leu Ile Glu Glu Ser Gln Asn Gln Gln
 1               5                  10                  15

Glu Lys Asn Glu Gln Glu Leu Leu Glu Phe Asp Lys Trp Ala Ser Leu
            20                  25                  30

Trp Asn Trp Phe
        35

<210> SEQ ID NO 49
<211> LENGTH: 36
<212> TYPE: PRT
<213> ORGANISM: Human immunodeficiency virus

<400> SEQUENCE: 49

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Pro Ala Ser Leu
            20                  25                  30

Trp Asn Trp Phe
        35

<210> SEQ ID NO 50
<211> LENGTH: 36
<212> TYPE: PRT
<213> ORGANISM: Human immunodeficiency virus

<400> SEQUENCE: 50

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Pro
            20                  25                  30

Trp Asn Trp Phe
        35

<210> SEQ ID NO 51
<211> LENGTH: 36
<212> TYPE: PRT

<213> ORGANISM: Human immunodeficiency virus

<400> SEQUENCE: 51

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Ser Phe
        35

<210> SEQ ID NO 52
<211> LENGTH: 36
<212> TYPE: PRT
<213> ORGANISM: Human immunodeficiency virus

<400> SEQUENCE: 52

Leu Leu Asp Asn Phe Glu Ser Thr Trp Glu Gln Ser Lys Glu Leu Trp
 1               5                  10                  15

Glu Gln Gln Glu Ile Ser Ile Gln Asn Leu His Lys Ser Ala Leu Gln
            20                  25                  30

Glu Tyr Trp Asn
        35

<210> SEQ ID NO 53
<211> LENGTH: 36
<212> TYPE: PRT
<213> ORGANISM: Human immunodeficiency virus

<400> SEQUENCE: 53

Leu Ser Asn Leu Leu Gln Ile Ser Asn Asn Ser Asp Glu Trp Leu Glu
 1               5                  10                  15

Ala Leu Glu Ile Glu His Glu Lys Trp Lys Leu Thr Gln Trp Gln Ser
            20                  25                  30

Tyr Glu Gln Phe
        35

<210> SEQ ID NO 54
<211> LENGTH: 63
<212> TYPE: PRT
<213> ORGANISM: Human immunodeficiency virus

<400> SEQUENCE: 54

Met Thr Leu Thr Val Gln Ala Arg Gln Leu Leu Ser Gly Ile Val Gln
 1               5                  10                  15

Gln Gln Asn Asn Leu Leu Arg Ala Ile Glu Ala Gln Gln His Leu Leu
            20                  25                  30

Gln Leu Thr Val Trp Gly Ile Lys Gln Leu Gln Ala Arg Ile Leu Ala
        35                  40                  45

Val Glu Arg Tyr Leu Lys Asp Gln Gln Leu Leu Gly Ile Trp Gly
    50                  55                  60

<210> SEQ ID NO 55
<211> LENGTH: 35
<212> TYPE: PRT
<213> ORGANISM: Human immunodeficiency virus

<400> SEQUENCE: 55

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu 20          25          30

Leu Leu Glu
        35

<210> SEQ ID NO 56
<211> LENGTH: 36
<212> TYPE: PRT
<213> ORGANISM: Human immunodeficiency virus

<400> SEQUENCE: 56

His Ser Leu Ile Glu Glu Ser Gln Asn Gln Gln Glu Lys Asn Glu Gln
 1               5                  10                  15

Glu Leu Leu Glu Leu Asp Lys Trp Ala Ser Leu Trp Asn Trp Phe Asn
            20                  25                  30

Ile Thr Asn Trp
        35

<210> SEQ ID NO 57
<211> LENGTH: 36
<212> TYPE: PRT
<213> ORGANISM: Human immunodeficiency virus

<400> SEQUENCE: 57

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
            20                  25                  30

Phe Asn Ile Thr
        35

<210> SEQ ID NO 58
<211> LENGTH: 36
<212> TYPE: PRT
<213> ORGANISM: Human immunodeficiency virus

<400> SEQUENCE: 58

Ser Leu Ile His Ser Leu Ile Glu Glu Ser Gln Asn Gln Gln Glu Lys
 1               5                  10                  15

Asn Glu Gln Glu Leu Leu Glu Leu Asp Lys Trp Ala Ser Leu Trp Asn
            20                  25                  30

Trp Phe Asn Ile
        35

<210> SEQ ID NO 59
<211> LENGTH: 36
<212> TYPE: PRT
<213> ORGANISM: Human immunodeficiency virus

<400> SEQUENCE: 59

Thr Ser Leu Ile His Ser Leu Ile Glu Glu Ser Gln Asn Gln Gln Glu
 1               5                  10                  15

Lys Asn Glu Gln Glu Leu Leu Glu Leu Asp Lys Trp Ala Ser Leu Trp
            20                  25                  30

Asn Trp Phe Asn
        35

<210> SEQ ID NO 60
<211> LENGTH: 36
<212> TYPE: PRT
<213> ORGANISM: Human immunodeficiency virus -continued

```
<400> SEQUENCE: 60

Asn Tyr Thr Ser Leu Ile His Ser Leu Ile Glu Ser Gln Asn Gln
 1               5                  10                  15

Gln Glu Lys Asn Glu Gln Glu Leu Leu Glu Leu Asp Lys Trp Ala Ser
             20                  25                  30

Leu Trp Asn Trp
         35

<210> SEQ ID NO 61
<211> LENGTH: 36
<212> TYPE: PRT
<213> ORGANISM: Human immunodeficiency virus

<400> SEQUENCE: 61

Asn Asn Tyr Thr Ser Leu Ile His Ser Leu Ile Glu Glu Ser Gln Asn
 1               5                  10                  15

Gln Gln Glu Lys Asn Glu Gln Glu Leu Leu Glu Leu Asp Lys Trp Ala
             20                  25                  30

Ser Leu Trp Asn
         35

<210> SEQ ID NO 62
<211> LENGTH: 36
<212> TYPE: PRT
<213> ORGANISM: Human immunodeficiency virus

<400> SEQUENCE: 62

Asp Arg Glu Ile Asn Asn Tyr Thr Ser Leu Ile His Ser Leu Ile Glu
 1               5                  10                  15

Glu Ser Gln Asn Gln Gln Glu Lys Asn Glu Gln Glu Leu Leu Glu Leu
             20                  25                  30

Asp Lys Trp Ala
         35

<210> SEQ ID NO 63
<211> LENGTH: 36
<212> TYPE: PRT
<213> ORGANISM: Human immunodeficiency virus

<400> SEQUENCE: 63

Trp Asp Arg Glu Ile Asn Asn Tyr Thr Ser Leu Ile His Ser Leu Ile
 1               5                  10                  15

Glu Glu Ser Gln Asn Gln Gln Glu Lys Asn Glu Gln Glu Leu Leu Glu
             20                  25                  30

Leu Asp Lys Trp
         35

<210> SEQ ID NO 64
<211> LENGTH: 36
<212> TYPE: PRT
<213> ORGANISM: Human immunodeficiency virus

<400> SEQUENCE: 64

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu Leu
             20                  25                  30

Glu Leu Asp Lys
         35
```

<210> SEQ ID NO 65
<211> LENGTH: 36
<212> TYPE: PRT
<213> ORGANISM: Human immunodeficiency virus

<400> SEQUENCE: 65

Met Glu Trp Asp Arg Glu Ile Asn Asn Tyr Thr Ser Leu Ile His Ser
 1               5                  10                  15

Leu Ile Glu Glu Ser Gln Asn Gln Gln Glu Lys Asn Glu Gln Glu Leu
             20                  25                  30

Leu Glu Leu Asp
         35

<210> SEQ ID NO 66
<211> LENGTH: 36
<212> TYPE: PRT
<213> ORGANISM: Human immunodeficiency virus

<400> SEQUENCE: 66

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
             20                  25                  30

Leu Leu Glu Leu
         35

<210> SEQ ID NO 67
<211> LENGTH: 36
<212> TYPE: PRT
<213> ORGANISM: Human immunodeficiency virus

<400> SEQUENCE: 67

Thr Trp Met Glu Trp Asp Arg Glu Ile Asn Asn Tyr Thr Ser Leu Ile
 1               5                  10                  15

His Ser Leu Ile Glu Glu Ser Gln Asn Gln Gln Glu Lys Asn Glu Gln
             20                  25                  30

Glu Leu Leu Glu
         35

<210> SEQ ID NO 68
<211> LENGTH: 36
<212> TYPE: PRT
<213> ORGANISM: Human immunodeficiency virus

<400> SEQUENCE: 68

Asn Met Thr Trp Met Glu Trp Asp Arg Glu Ile Asn Asn Tyr Thr Ser
 1               5                  10                  15

Leu Ile His Ser Leu Ile Glu Glu Ser Gln Asn Gln Gln Glu Lys Asn
             20                  25                  30

Glu Gln Glu Leu
         35

<210> SEQ ID NO 69
<211> LENGTH: 36
<212> TYPE: PRT
<213> ORGANISM: Human immunodeficiency virus

<400> SEQUENCE: 69

Asn Asn Met Thr Trp Met Glu Trp Asp Arg Glu Ile Asn Asn Tyr Thr
 1               5                  10                  15

```
Ser Leu Ile His Ser Leu Ile Glu Glu Ser Gln Asn Gln Gln Glu Lys
            20                  25                  30

Asn Glu Gln Glu
        35

<210> SEQ ID NO 70
<211> LENGTH: 36
<212> TYPE: PRT
<213> ORGANISM: Human immunodeficiency virus

<400> SEQUENCE: 70

Trp Asn Asn Met Thr Trp Met Glu Trp Asp Arg Glu Ile Asn Asn Tyr
 1               5                  10                  15

Thr Ser Leu Ile His Ser Leu Ile Glu Glu Ser Gln Asn Gln Gln Glu
            20                  25                  30

Lys Asn Glu Gln
        35

<210> SEQ ID NO 71
<211> LENGTH: 36
<212> TYPE: PRT
<213> ORGANISM: Human immunodeficiency virus

<400> SEQUENCE: 71

Gln Ile Trp Asn Asn Met Thr Trp Met Glu Trp Asp Arg Glu Ile Asn
 1               5                  10                  15

Asn Tyr Thr Ser Leu Ile His Ser Leu Ile Glu Glu Ser Gln Asn Gln
            20                  25                  30

Gln Glu Lys Asn
        35

<210> SEQ ID NO 72
<211> LENGTH: 35
<212> TYPE: PRT
<213> ORGANISM: Human immunodeficiency virus

<400> SEQUENCE: 72

Trp Gln Glu Trp Glu Arg Lys Val Asp Phe Leu Glu Glu Asn Ile Thr
 1               5                  10                  15

Ala Leu Leu Glu Glu Ala Gln Ile Gln Gln Glu Lys Asn Met Tyr Glu
            20                  25                  30

Leu Gln Lys
        35

<210> SEQ ID NO 73
<211> LENGTH: 35
<212> TYPE: PRT
<213> ORGANISM: Human immunodeficiency virus

<400> SEQUENCE: 73

Gln Glu Trp Glu Arg Lys Val Asp Phe Leu Glu Glu Asn Ile Thr Ala
 1               5                  10                  15

Leu Leu Glu Glu Ala Gln Ile Gln Gln Glu Lys Asn Met Tyr Glu Leu
            20                  25                  30

Gln Lys Leu
        35

<210> SEQ ID NO 74
<211> LENGTH: 35
<212> TYPE: PRT
<213> ORGANISM: Human immunodeficiency virus
```

<400> SEQUENCE: 74

Glu Trp Glu Arg Lys Val Asp Phe Leu Glu Glu Asn Ile Thr Ala Leu
1               5                   10                  15

Leu Glu Glu Ala Gln Ile Gln Gln Glu Lys Asn Met Tyr Glu Leu Gln
            20                  25                  30

Lys Leu Asn
        35

<210> SEQ ID NO 75
<211> LENGTH: 35
<212> TYPE: PRT
<213> ORGANISM: Human immunodeficiency virus

<400> SEQUENCE: 75

Trp Glu Arg Lys Val Asp Phe Leu Glu Glu Asn Ile Thr Ala Leu Leu
1               5                   10                  15

Glu Glu Ala Gln Ile Gln Gln Glu Lys Asn Met Tyr Glu Leu Gln Lys
            20                  25                  30

Leu Asn Ser
        35

<210> SEQ ID NO 76
<211> LENGTH: 35
<212> TYPE: PRT
<213> ORGANISM: Human immunodeficiency virus

<400> SEQUENCE: 76

Glu Arg Lys Val Asp Phe Leu Glu Glu Asn Ile Thr Ala Leu Leu Glu
1               5                   10                  15

Glu Ala Gln Ile Gln Gln Glu Lys Asn Met Tyr Glu Leu Gln Lys Leu
            20                  25                  30

Asn Ser Trp
        35

<210> SEQ ID NO 77
<211> LENGTH: 35
<212> TYPE: PRT
<213> ORGANISM: Human immunodeficiency virus

<400> SEQUENCE: 77

Arg Lys Val Asp Phe Leu Glu Glu Asn Ile Thr Ala Leu Leu Glu Glu
1               5                   10                  15

Ala Gln Ile Gln Gln Glu Lys Asn Met Tyr Glu Leu Gln Lys Leu Asn
            20                  25                  30

Ser Trp Asp
        35

<210> SEQ ID NO 78
<211> LENGTH: 35
<212> TYPE: PRT
<213> ORGANISM: Human immunodeficiency virus

<400> SEQUENCE: 78

Lys Val Asp Phe Leu Glu Glu Asn Ile Thr Ala Leu Leu Glu Glu Ala
1               5                   10                  15

Gln Ile Gln Gln Glu Lys Asn Met Tyr Glu Leu Gln Lys Leu Asn Ser
            20                  25                  30

Trp Asp Val
        35

```
<210> SEQ ID NO 79
<211> LENGTH: 35
<212> TYPE: PRT
<213> ORGANISM: Human immunodeficiency virus

<400> SEQUENCE: 79

Val Asp Phe Leu Glu Glu Asn Ile Thr Ala Leu Leu Glu Glu Ala Gln
 1               5                  10                  15

Ile Gln Gln Glu Lys Asn Met Tyr Glu Leu Gln Lys Leu Asn Ser Trp
            20                  25                  30

Asp Val Phe
        35

<210> SEQ ID NO 80
<211> LENGTH: 35
<212> TYPE: PRT
<213> ORGANISM: Human immunodeficiency virus

<400> SEQUENCE: 80

Asp Phe Leu Glu Glu Asn Ile Thr Ala Leu Leu Glu Glu Ala Gln Ile
 1               5                  10                  15

Gln Gln Glu Lys Asn Met Tyr Glu Leu Gln Lys Leu Asn Ser Trp Asp
            20                  25                  30

Val Phe Gly
        35

<210> SEQ ID NO 81
<211> LENGTH: 35
<212> TYPE: PRT
<213> ORGANISM: Human immunodeficiency virus

<400> SEQUENCE: 81

Phe Leu Glu Glu Asn Ile Thr Ala Leu Leu Glu Glu Ala Gln Ile Gln
 1               5                  10                  15

Gln Glu Lys Asn Met Tyr Glu Leu Gln Lys Leu Asn Ser Trp Asp Val
            20                  25                  30

Phe Gly Asn
        35

<210> SEQ ID NO 82
<211> LENGTH: 38
<212> TYPE: PRT
<213> ORGANISM: Human immunodeficiency virus

<400> SEQUENCE: 82

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile Leu Ala Val Glu
            20                  25                  30

Arg Tyr Leu Lys Asp Gln
        35
```

TREATMENT OF HIV AND OTHER VIRAL INFECTIONS USING COMBINATORIAL THERAPY

This application is the U.S. national phase under U.S.C. § 371 of international application No. PCT/US96/09499, filed Jun. 6, 1996 which is a continuation-in-part of application Ser. No. 08/481,957, filed Jun. 7, 1995 now abandoned.

1. FIELD OF THE INVENTION

The present invention relates to methods of treating viral infections, particularly HIV infection, using novel combinational therapy. The novel combinational therapy employs either the peptide DP-178, DP-107 or fragments, analogs and/or homologs thereof, and at least one other therapeutic agent.

DP-178 is a peptide corresponding to amino acids 638 to 673 of the HIV-$1_{LA1}$ transmembrane protein (TM) gp41. DP-178 includes portions, analogs, and homologs of DP-178, all of which exhibit antiviral activity. Antiviral activity includes, but is not limited to, the inhibition of HIV transmission to uninfected CD-4+ cells. Further, the invention relates to the use of DP-178 and DP-178 fragments and/or analogs or homologs as inhibitors of retroviral transmission, in particular HIV, to uninfected cells, in both humans and non-humans. The present invention also relates to the antiviral peptide DP-107, a peptide corresponding to amino acids 558 to 595 of the HIV-$1_{LA1}$ transmembrane protein (TM) gp41, that are present in other enveloped viruses. More specifically, the invention is directed to the use of DP-107, fragments and/or analogs or homologs in combination with other therapeutic agents to treat viral infections, particularly HIV infection. Further, the invention encompasses novel pharmaceutical compositions comprising DP-178 or DP-107 and at least one other therapeutic agent.

2. BACKGROUND OF THE INVENTION

2.1. The Human Immunodeficiency Virus

The human immunodeficiency virus (HIV) is a pathogenic retrovirus and the causative agent of acquired immune deficiency syndrome (AIDS) and related disorders (Barre-Sinossi, F. et al., 1983, Science 220:868–870; Gallo, R. et al., 1984, Science 224:500–503). There are at least two distinct types of HIV: HIV-1 (Barre-Sinossi, F. et al., 1983, Science 220:868–870; Gallo, R. et al., 1984, Science 224:500–503) and HIV-2 (Clavel, F. et al., 1986, Science 223:343–346; Guyader, M. et al., 1987, Nature 326:662–669). Further, a large amount of genetic heterogeneity exists within populations of each of these types. Infection of human CD-4+ T-lymphocytes with an HIV virus leads to depletion of the cell type and eventually to opportunistic infections, neurological dysfunctions, neoplastic growth, and untimely death.

HIV is a member of the lentivirus family of retroviruses (Teich, N. et al., 1984; RNA Tumor Viruses, Weiss, R. et al., eds., CSH-press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, H., 1988, Science 240:1427–1439). Other retroviruses include, for example, oncogenic viruses such as human T-cell leukemia viruses (HTLV-1,-II,-III), and feline leukemiavirus. The HIV viral particle consists of a viral core, made up of proteins designated p24 and p18. The viral core contains the viral RNA genome and those enzymes required for replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains noncovalently associated with gp41, possibly in a trimeric or multimeric form (Hammerwskjold, M. and Rekosh, D., 1989, Biochem. Biophys. Acta 989:269–280).

HIV is targeted to CD-4+ T lymphocytes because the CD-4 surface protein acts as the cellular receptor for the HIV-1 virus (Dalgleish, A. et al., 1984, Nature 312:767–768, Maddon et al., 1986, Cell 47:333–348). Viral entry into cells is dependent upon gp120 binding the cellular CD-4+receptor molecules, while gp41 anchors the envelope glycoprotein complex in the viral membrane (McDougal, J. S. et al., 1986, Science 231:382–385; Maddon, P. J. et al., 1986, Cell 47:333–348) and thus explains HIV's tropism for CD-4+ cells.

2.2. HIV Treatment

HIV infection is pandemic and HIV associated diseases represent a major world health problem. Although considerable effort is being put into the successful design of effective therapeutics, currently no curative anti-retroviral drugs against AIDS exist. In attempts to develop such drugs, several stages of the viral life cycle have been considered as targets for therapeutic intervention (Mitsuya, H. et al., 1991, FASEB J. 5:2369–2381). Intervention could potentially inhibit the binding of HIV to cell membranes, the reverse transcription of HIV RNA genome into DNA or the exit of the virus from the host cell and infection of new cellular targets.

Attempts are being made to develop drugs which can inhibit viral entry into the cell, the earliest stage of HIV infection. Here, the focus has been on CD-4+, the cell surface receptor for HIV. For example, recombinant soluble CD-4 has been shown to block HIV infectivity by binding to viral particles before they encounter CD-4 molecules embedded in cell membranes (Smith, D. H. et al., 1987, Science 238:1704–1707). Certain primary HIV-1 isolates are relatively less sensitive to inhibition by recombinant CD-4 (Daar, E. et al., 1990, Ann. Int. Med. 112:247–253). In addition, recombinant soluble CD-4 clinical trials have produced inconclusive results (Schooley, R. et al., 1990, Ann. Int. Med. 112:247–253; Kahn, J. O. et al., 1990, Ann. Int. Med. 112:254–261; Yarchoan, R. et al., 1989, Proc. Vth Int. Conf. on AIDS, p564, MCP 137).

The virally encoded reverse-transcriptase-targeted drugs, including 2',3'-dideoxynucleoside analogs such as AZT, ddI, ddC, and d4T, have been developed which have also been shown to be active against HIV (Mitsuya, H. et al., 1991, Science 249:1533–1544). While beneficial, these nucleoside analogs are not curative, probably due to the rapid appearance of drug resistant HIV mutants (Lander, B. et al., 1989, Science 243:1731–1734). In addition, the drugs often exhibit toxic side effects such as bone marrow suppression, vomiting, and liver function abnormalities.

The late stages of HIV replication, which involve crucial virus-specific secondary processing of certain viral proteins, have also been suggested as possible anti-HIV drug targets.

Late stage processing is dependent on the activity of a viral protease, and drugs are being developed which inhibit this protease (Erikson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, Science 228:1094–1096). Thus far, these proteins seem to be the most promising candidates to act as antigens for anti-HIV development. To this end, several groups have begun to use various portions of gp16O, gp120, and/or gp41 as immunogenic targets for the host immune systems. See for example, Ivanoff, L. et al., U.S. Pat. No. 5,141,867; Saith, G. et al., WO 92/22, 654; Schafferman, A., WO 91/09,872; Formoso, C. et al., WO 90/07,119. Clinical results concerning these candidate vaccines, however, still remain far in the future.

Recently, double stranded RNAs, which elicit a general immune response; have been used in combination with antivirals such as interferon, AZT and phosphonoformate to treat viral infections. See Carter, W., U.S. Pat. No. 4,950, 652. In addition, a therapy combining a pyrimidine nucleoside analog and a uridine phosphorylase inhibitor has been developed for the treatment of HIV, see Sommadossi, J. P. et al., U.S. Pat. No. 5,077,280. Although these specific therapies may prove to be beneficial, combination therapy in general has the potential for antagonism as demonstrated in vitro with azidothymidine (AZT) and ribavirin. See U.S. Pat. No. 4,950,652. Moreover, combination therapy is potentially problematic given the high toxicity of most anti-HIV therapeutics and their low level of effectiveness. Thus, there is a need for a combination therapy which is effective yet non-toxic.

The present invention provides a novel combination therapy based on the use of viral fusion inhibitors (DP-178 and DP-107, etc.) in combination with other antivirals. DP-178 and DP-107 are both novel therapeutics in that they prevent the virus from fusing with the cell, thereby very effectively preventing cell to cell transmission of the virus. In addition, DP-178 and DP-107 have proven to be non-toxic in in vitro studies and in animals. The present invention provides the first reported use of such peptides in combination with another antiviral or any other therapeutic agent.

3. SUMMARY OF THE INVENTION

The present invention relates to methods of treating or preventing viral infections, in particular HIV infections, in mammals, including humans, by administering an effective amount of DP-178, or a pharmaceutically acceptable derivative thereof in combination with at least one other therapeutic agent.

The present invention also relates to methods of treating or preventing viral infections, in particular HIV infections, in mammals, including humans, by administering an effective amount of DP-107 or pharmaceutically acceptable derivatives thereof in combination with at least one other therapeutic agent.

More specifically, the invention relates to methods of treating or preventing viral infections in mammals, including humans, by administering an effective amount of DP-107, DP-178, or a pharmaceutically acceptable derivative thereof, in combination with at least one other antiviral agent. The invention includes the administration of the active agents, e.g., DP-107, DP-178 or another antiviral either concomitantly or sequentially, including cycling therapy. Cycling therapy involves the administration of a first antiviral compound for a period of time, followed by the administration of a second antiviral compound for a period of time and repeating this sequential administration, i.e., the cycle, in order to reduce the development of resistance to one of the therapies. The invention encompasses combinations of DP-107, DP-178 or a pharmaceutically acceptable derivative thereof and at least one other therapeutic, particularly another antiviral, that are synergistic, i.e., better than either agent or therapy alone.

The invention also encompasses combinations of DP-178, DP-107 or a pharmaceutically acceptable derivative thereof with a least one other antiviral having a different site of action than the viral fusion inhibitor. Such a combination provides an improved therapy based on the dual action of these therapeutics whether the combination is synergistic or additive.

The present invention is also directed to methods of treating or preventing HIV infection in mammals, including humans, by administering an effective amount of DP-107, DP-178 or a pharmaceutically acceptable derivative thereof in combination with at least one other therapeutic agent, in particular at least one other antiviral.

The novel antiviral combinations of the present invention provide a means of treatment which may not only reduce the effective dose of either drug required for antiviral activity, thereby reducing toxicity, but may also improve the absolute antiviral effect as a result of attacking the virus through multiple mechanisms. Similarly, the novel antiviral combinations provide a means for circumventing the development of viral resistance to a single therapy, thereby providing the clinician with a more efficacious treatment.

Another aspect of the invention encompasses pharmaceutical compositions and formulations for treating or preventing viral infections, in particular HIV infections, wherein said compositions comprise an effective amount of DP-178, DP-107, or a pharmaceutically acceptable derivative thereof, at least one additional therapeutic agent and a pharmaceutically acceptable carrier.

Therapeutic agents to be used in combination with DP-178, DP-107 or a pharmaceutically acceptable derivative thereof encompass a wide variety of known treatments. Preferably, the combinations employ DP-107 or DP-178 in combination with agents with a different mode of attack. Such agents include but are not limited to: antivirals, such as cytokines, e.g., rIFN α, rIFN β, rIFN γ; inhibitors of reverse transcriptase, e.g., AZT, 3TC, D4T, ddI, and other dideoxynucleosides or dideoxyfluoronucleosides; inhibitors of viral mRNA capping, such as ribavirin; inhibitors of HIV protease, such as ABT-538 and MK-639; amphotericin B as a lipid-binding molecule with anti-HIV activity; and castanospermine as an inhibitor of glycoprotein processing.

Thus, the present invention provides an improved antiviral therapy for treating a broad spectrum of viruses including HIV.

The present invention also provides combinational therapy which yields improved efficacy over either agent used as a single-agent therapy.

In addition, the invention provides combinational therapy which allows for reduced toxicity of DP-178 and DP-107 and/or the therapeutic agent with which the peptides are used; thereby providing a higher therapeutic index.

The instant invention provides a combinational therapy which provides a means for circumventing the development of viral resistance to a single therapy.

3.1. Definitions

As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating or preventing viral infections" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

The term "synergistic" as used herein refers to a combination which is more effective than the additive effects of any two or more single agents. A synergistic effect as used herein refers to the ability to use lower amounts (doses) of either single therapy to treat or prevent viral infection. The lower doses result in lower toxicity without reduced efficacy. In addition, a synergistic effect can result in improved efficacy, i.e., improved antiviral activity. Finally, synergy may result in an improved avoidance or reduction of viral resistance against any single therapy. A determination of a synergistic interaction between DP-178 or DP-107, and another therapeutic agent may be based on the results obtained from the antiviral assays described in Section 5.5. The results of these assays are analyzed using Chou and Talalay's combination method (Chou and Talalay, 1984, Adv. Enzyme Regul. 22:27–55) and 'Dose-Effect Analysis with Microcomputers' software (Chou and Chou, 1987, software and manual. p19–64. Elsevier Biosoft, Cambridge, UK) in order to obtain a Combination Index. Combination Index values <1 indicates synergy, values>1 indicate antagonism and values equal to 1 indicate additive effects.

The results of these assays are also analyzed using the method of Pritchard and Shipman (Pritchard and Shipman, 1990, *Antiviral Research* 14: 181–206). This computer program through three dimensional graphic analysis of the results allows for a determination of a synergistic or antagonistic interaction between the antiviral agents.

The term "pharmaceutically acceptable carrier" refers to a carrier medium that does not interfere with the effectiveness of the biological activity of the active ingredient, is chemically inert and is not toxic to the patient to whom it is administered.

As used herein the term "pharmaceutically acceptable derivative" refers to any homolog, analog, or fragment corresponding to the DP-178 or DP-107 peptides as described in Section 5.1.2. infra which exhibits antiviral activity and is relatively non-toxic to the subject.

The term "therapeutic agent" refers to any molecule, compound or treatment, preferably an antiviral, that assists in the treatment of a viral infection or the diseases caused thereby.

Peptides are defined herein as organic compounds comprising two or more amino acids covalently joined by peptide bonds. Peptides may be referred to with respect to the number of constituent amino acids, i e., a dipeptide contains two amino acid residues, a tripeptide contains three, etc. Peptides containing ten or fewer amino acids may be referred to as oligopeptides, while those with more than ten amino acid residues are polypeptides.

Peptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)

4. BRIEF DESCRIPTION OF THE FIGURES

FIG. 1. Amino acid sequence of DP-178 (SEQ ID:1) derived from $HIV_{LA1}$; DP-178 homologs derived from $HIV-1_{SF2}$ (DP-185; SEQ ID:3), $HIV-1_{RF}$ (SEQ ID:4), and $HIV-1_{MN}$ (SEQ ID:5); DP-178 homologs derived from amino acid sequences of two prototypic HIV-2 isolates, namely, $HIV-2_{rod}$ (SEQ ID:6) and $HIV-2_{NIHZ}$ (SEQ ID:7); control peptides: DP-180 (SEQ ID:2), a peptide incorporating the amino acid residues of DP-178 in a scrambled sequence; DP-118 (SEQ ID:10) unrelated to DP-178, which inhibits HIV-1 cell free virus infection; DP-125 (SEQ ID:8), unrelated to DP-178, was also previously shown to inhibit HIV-1 cell free virus infection (Wild et al., 1992, Proc. Natl. Acad. Sci. USA 89:10, 537–10,541); DP-116 (SEQ ID:9), unrelated to DP-178 had previously been shown to be negative for inhibition of HIV-1 infection using the cell-free virus infection assay (Wild, et al., 1992, Proc. Natl. Acad. Sci USA 89:10,537–10, 541). Throughout the figures, the one letter amino acid code is used.

FIG. 2. Inhibition of HIV-1 cell-free virus infection by synthetic peptides. IC50 refers to the concentration of peptide that inhibits RT production from infected cells by 50% compared to the untreated control. Control: the level of RT produced by untreated cell cultures infected with the same level of virus as treated cultures.

Figure 3:
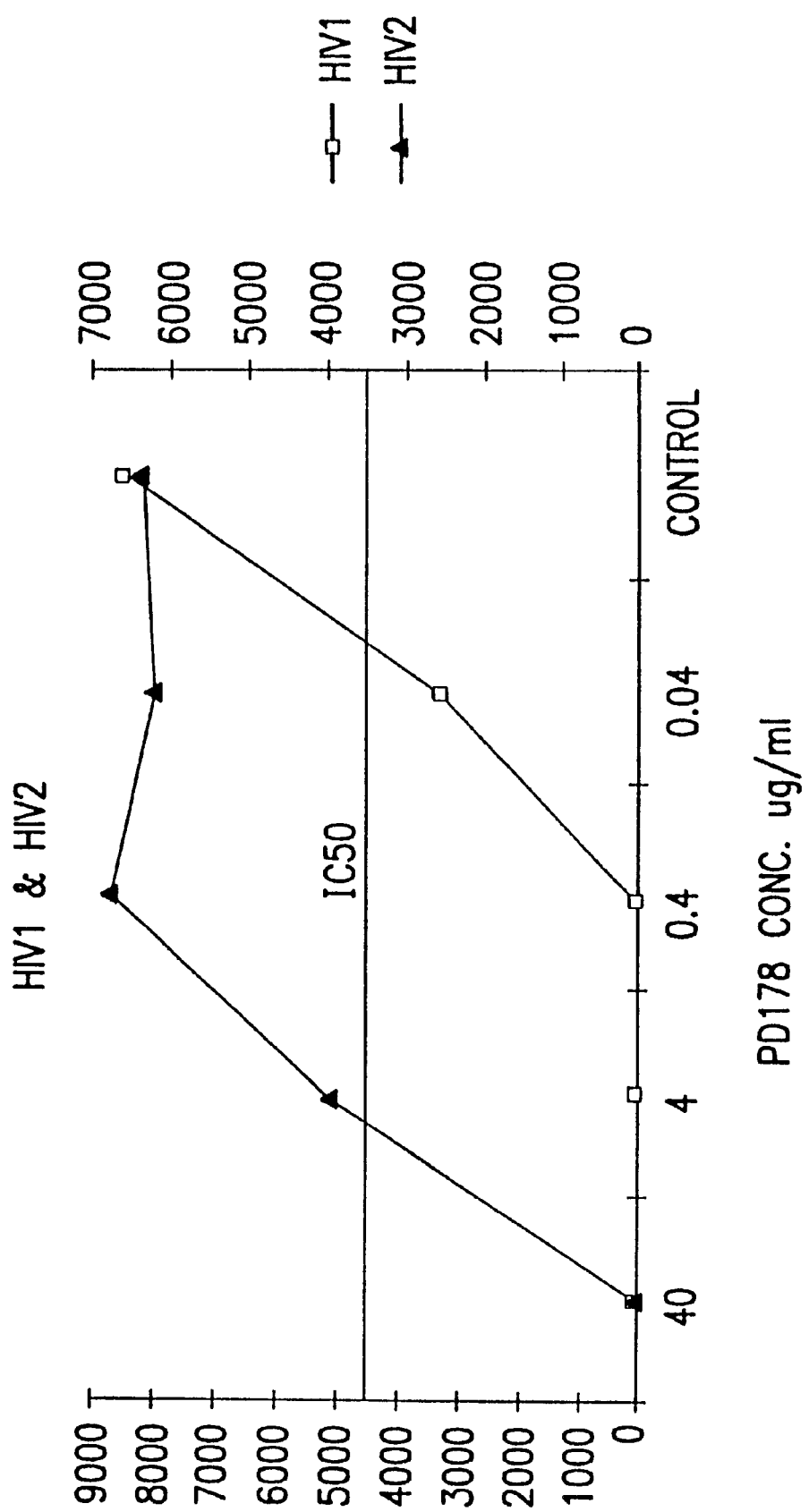

FIG. 3. Inhibition of HIV-1 and HIV-2 cell-free virus infection by the synthetic peptide DP-178 (SEQ ID:1). IC50: concentration of peptide necessary to inhibit RT production by 50% compared to the untreated control. Control: Level of RT produced by untreated cell cultures infected with the same level of virus as treated cultures.

Figure 4:
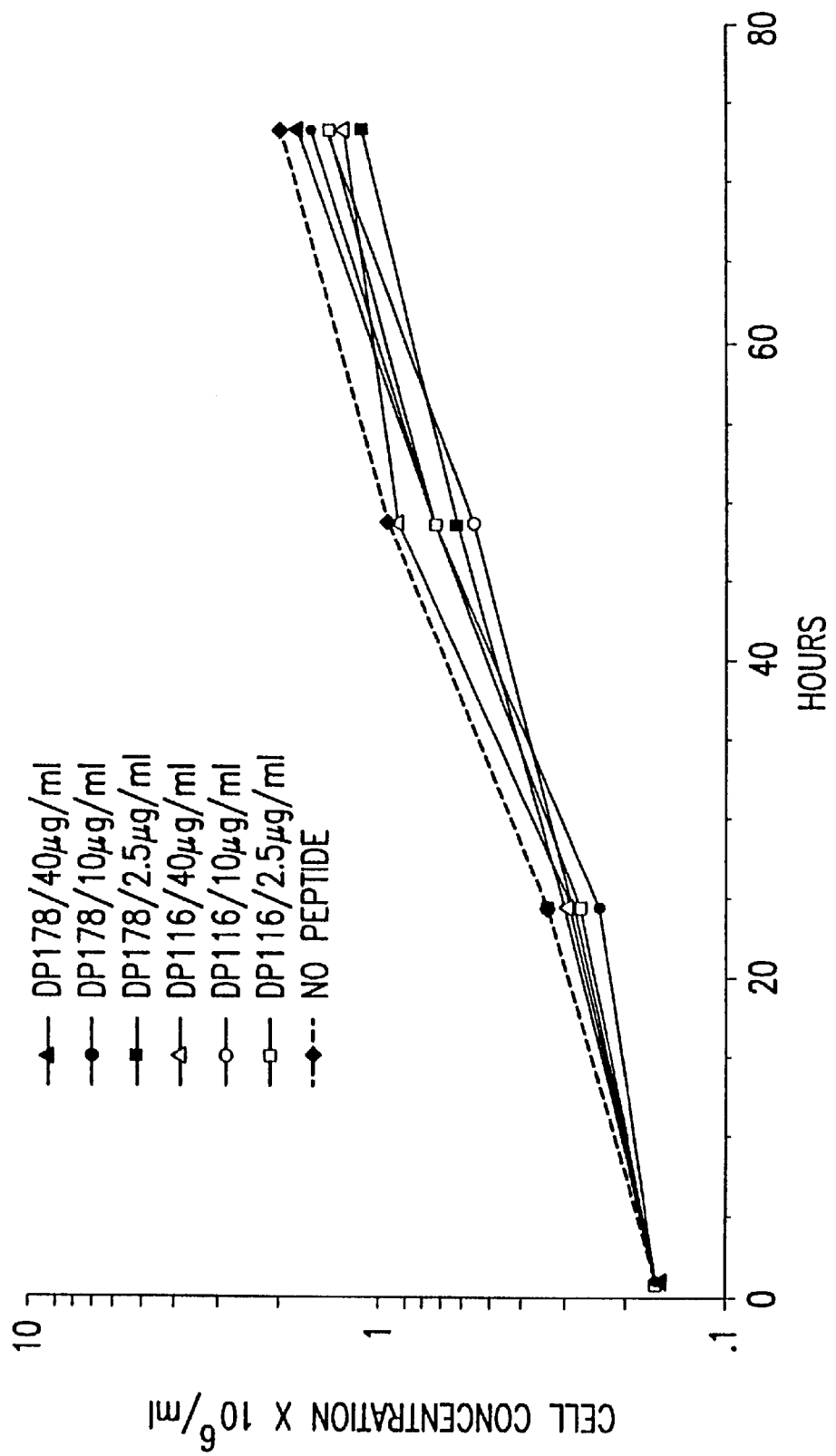

FIG. 4. Cytotoxicity study of DP-178 (SEQ ID:1) and DP-116 (SEQ ID:9) on CEM cells. Cell proliferation data is shown.

FIGS. 5A–5L. DP178-derived peptide antiviral data [(SEQ ID NO:11); T50:(SEQ ID NO:12); (SEQ ID NO:13); T234:(SEQ ID NO:14); T235:(SEQ ID NO:15); T570:(SEQ ID NO:16); T381:(SEQ ID NO:17); T677:(SEQ ID NO:18); T589:(SEQ ID NO:19); T590:(SEQ ID NO:20); T591:(SEQ ID NO:21); T270:(SEQ ID NO:22); T271:(SEQ ID NO:23); T273:(SEQ ID NO:24); T608:(SEQ ID NO:25); T609:(SEQ ID NO:26); T610:(SEQ ID NO:27); T611:(SEQ ID NO:28); T612:(SEQ ID NO:29); T595:(SEQ ID NO:30); T95:(SEQ ID NO:31); T96:(SEQ ID NO:32); T97:(SEQ ID NO:33); T98:(SEQ ID NO:34); T99:(SEQ ID NO:35); T103:(SEQ ID NO:36); T212:(SEQ ID NO:37); T213:(SEQ ID NO:38); T214:(SEQ ID NO:39); T215:(SEQ ID NO:40); T216:(SEQ ID NO:41); T229:(SEQ ID NO:42); T230:(SEQ ID NO:43); T231:(SEQ ID NO:44); T379:(SEQ ID NO:45); T701:(SEQ ID NO:46); T702:(SEQ ID NO:47); T703:(SEQ ID NO:48); T704:(SEQ ID NO:49); T705:(SEQ ID NO:50); T706:(SEQ ID NO:51); T156:(SEQ ID NO:52); T90:(SEQ ID NO:53)]. The peptides listed herein were derived from the region surrounding the HIV-1 BRU isolate DP178 region (e.g., gp41 amino acid residues 615–717). In instances where peptides contained DP178 point mutations, the mutated amino acid residues are shown with a shaded background. In instances in which the test peptide has had an amino and/or carboxy-terminal group added or removed (apart from the standard amido- and acetyl-blocking groups found on such peptides), such modifications are indicated.

FIGS. 5A–5D. The column to the immediate right of the name of the test peptide indicates the size of the test peptide and points out whether the peptide is derived from a one amino acid peptide "walk" across the DP178 region. The next column to the right indicates whether the test peptide contains a point mutation, while the column to its right indicates whether certain amino acid residues have been added to or removed from the DP178-derived amino acid sequence.

FIGS. 5E–5H. The column to the immediate right of the test peptide name indicates whether the peptide represents a DP178 truncation, the next column to the right points out whether the peptide contains a point mutation, and the column to its right indicates whether the peptide contains amino acids which have been added to or removed from the DP178 sequence itself.

FIGS. 5I–5L. The column to the immediate right of the test peptide name indicates whether the test peptide contains a point mutation, while the column to its right indicates whether amino acid residues have been added to or removed from the DP178 sequence itself.

FIGS. 6A–6B. DP107 and DP107 gp41 region truncated peptide antiviral data. $IC_{50}$ values were obtained using purified peptides except where marked with an asterisk (*), in which case the $IC_{50}$ was obtained using a crude peptide preparation.

FIGS. 7A–7B. Simian immunodeficiency virus (SIV) TM (fusion) protein DP178-like region antiviral data. "NT" indicates "not tested."

5. DETAILED DESCRIPTION OF THE INVENTION

The invention relates to methods of treating HIV infection in mammals, including humans which comprises administering an effective amount of DP-107, DP-178 or a pharmaceutically acceptable derivative thereof and an effective amount of at least one other therapeutic agent. Preferably, the therapeutic agent is another antiviral agent.

The present method provides an improved treatment for viral infection, specifically HIV infection. Specifically, the invention provides synergistic combinations for the treatment of HIV infection which comprise an effective amount of DP-178, DP-107 or pharmaceutically acceptable derivatives thereof and at least one member of a wide range of antiviral compounds available for the treatment of viral diseases. DP-178, DP-107 or a pharmaceutically acceptable derivative thereof is preferably used in combination with retrovirus inhibitors, viral protease inhibitors, cytokines or cytokine inhibitors or viral fusion inhibitors. The combinations of the present invention are administered to a patient in an amount sufficient to inhibit viral activity, to inhibit viral expression, or to inhibit viral transmission.

The method of the invention encompasses combination therapy in which DP-178, DP-107 and at least one other therapeutic agent are administered either concomitantly, e.g., as an admixture, separately but simultaneously or concurrently; or sequentially, including cycling therapy. Cycling therapy involves the administration of a first antiviral compound for a period of time, followed by the administration of a second antiviral compound for a period of time and repeating this sequential administration, i.e., the cycle, in order to reduce the development of resistance to one of the therapies. The invention also encompasses cycling therapy which comprises the administration of a first peptide of the present invention, followed by another antiviral, followed by another peptide of the present invention, etc., such that both viral fusion inhibitors DP-107 and DP-178 or derivatives thereof are used in combination with other antivirals. The invention also encompasses the use of a combination of the peptides, e.g., DP-107 in combination with DP-178.

Administration of DP-178, DP-107 or a pharmaceutically acceptable derivative thereof and one or more therapeutics "in combination" includes presentations in which both agents are administered together as a therapeutic mixture, and also procedures in which the two agents are administered separately but simultaneously, e.g., as through separate intravenous lines into the same individual. Administration "in combination" further includes the separate administration of one of the drugs given first, followed by the second.

The Applicants' novel therapy involves the use of peptides which inhibit viral fusion and cell to cell transmission of the virus in combination with another therapeutic. Without being limited by theory, the present invention is based, in part, on the belief that HIV is believed to be replicating 24 hours a day from the first day of infection. Therefore it may be beneficial to use antiviral treatment at different stages of the viral infection.

The combinations disclosed herein present the first known use of viral fusion inhibitors, acting at the first stage of viral infection, in combination with antivirals having different targets of action.

The DP-178 and DP-107 site of action is at the surface of the virus, preventing free virus from infecting host cells and cell-cell transmission of the virus. Therefore, without being limited by theory, Applicants believe that DP-178 or DP-107 used in combination with one or more drugs having different targets or mechanisms of action provides either an additive or synergistic effect. The combinations of the present invention are advantageous in that the drugs employed will be used at lower, less toxic concentrations. Combination therapy may not only reduce the effective dose of a drug required for antiviral activity, thereby reducing its toxicity, but may also improve the absolute antiviral effect as a result of attacking the virus through multiple mechanisms. Finally, the combinations of the present invention also provide a means for circumventing or decreasing the chance of development of viral resistance.

The preferred treatments to be used in combination with DP-178 and/or DP-107 include but are not limited to five different modes of attack on the virus: inhibition of the reverse transcriptase, inhibition of viral mRNA capping, inhibition of the HIV protease, inhibition of protein glycosylation, and inhibition of viral fusion. Agents which employ these modes of attack include, but are not limited to, antivirals, such as cytokines, e.g., rIFN α, rIFN β, rIFN γ; inhibitors of reverse transcriptase, such as AZT, 3TC, D4T, ddI, and dideoxyfluoronucleosides; inhibitors of viral mRNA capping, such as ribavarin; inhibitors of HIV protease, such as ABT-538 and MK-639; amphotericin B as a lipid-binding molecule with anti-HIV activity; and castanospermine as an inhibitor of glycoprotein processing.

5.1. Treatment of HIV with DP-178 or DP-107
5.1.1. DP-178 and DP-107 Peptides DP-178 and DP-107 are peptides that exhibit potent antiviral activity by inhibiting virus fusion. These peptides include DP-178, a gp41 derived 36 amino acid peptide, fragments and/or analogs of DP-178, and peptides homologous to DP-178. In addition, these peptides may include peptides exhibiting antiviral activity which are analogous to DP-107, a 38 amino acid peptide, corresponding to residues 558 to 595 of the HIV-1$_{LA1}$ transmembrane gp41 protein, and which are present in other enveloped viral proteins. The use of the peptides of the invention as inhibitors of non-human and human and retroviral, especially HIV transmission are detailed herein and in U.S. patent application Ser. No. 08/073,028, filed Jun. 7, 1993, U.S. patent application Ser. No. 08/264,531, filed Jun. 23, 1994, U.S. patent application Ser. No. 08/255,208, filed Jun. 7, 1994, U.S. patent application Ser. No. 08/360,107, filed Dec. 20, 1994, U.S. patent application Ser. No. 08/374,666, filed Jan. 27, 1995, U.S. patent application Ser. No. 08/470,896, filed Jun. 6, 1995, and U.S. patent application Ser. No. 08/485,264, filed Jun. 7, 1995, which are incorporated by reference herein in their entirety.

While not limited to any theory of operation, the following model is proposed to explain the potent anti-HIV activity of DP-178. In the viral protein, gp41, DP-178 corresponds to a putative α-helix region located in the C-terminal end of the gp41 ectodomain, and appears to associate with a distal site on gp41 whose interactive structure is influenced by the leucine zipper motif, a coiled-coil structure, referred to as DP-107. The association of these two domains may reflect a molecular linkage or "molecular clasp" intimately involved in the fusion process. It may be that the leucine zipper motif is involved in membrane fusion while the C-terminal α-helix motif serves as a molecular safety mechanism to regulate the availability of the leucine zipper during virus induced membrane fusion.

When synthesized as peptides both DP-107 and DP-178 are potent inhibitors of HIV infection and fusion, probably by virtue of their ability to form complexes with viral gp41 and interfere with its fusogenic process; e.g., during the structural transition of the viral protein from the native structure to the fusogenic state, the DP-107 and DP-178 peptides may gain access to their respective binding sites on the viral gp41, and exert a disruptive influence.

A truncated recombinant gp41 protein corresponding to the ectodomain of gp41 containing both DP-107 and DP-178 domains (excluding the fusion peptide, transmembrane region and cytoplasmic domain of gp41) did not inhibit HIV-1 induced fusion. However when a single mutation was introduced to disrupt the coiled-coil structure of the DP-107 domain—a mutation which results in a total loss of biological activity of DP-107 peptides—the inactive recombinant protein was transformed to an active inhibitor of HIV-1 induced fusion. This transformation may result from liberation of the potent DP-178 domain from a molecular clasp with the leucine zipper, DP-107 domain.

The peptide DP-178 of the invention corresponds to amino acid residues 638 to 673 of the transmembrane protein gp41 from the HIV-1$_{LA1}$ isolate, and has the 36 amino acid sequence (reading from the amino to carboxy terminus):

NH2—YTSLIHSLIEESQNQQEKNEQELLELDKWA SLWNWF—COOH (SEQ ID:1)

DP-178 is also described in Applicant's co-pending U.S. patent applications Ser. No. 08/470,896, filed Jun. 6, 1995, Ser. No. 08/374,666, filed Jan. 27, 1995, Ser. No. 08/264,531, filed Jun. 23, 1994, and Ser. No. 08/255,208, filed Jun. 7, 1994, which are incorporated herein by reference in their entirety.

In addition to the full length DP-178 (SEQ ID:1) 36 mer, the peptides of the invention may include truncations of the DP-178 (SEQ ID:1) peptide which exhibit antiviral activity. Such truncated DP-178 (SEQ ID:1) peptides may comprise peptides of between 3 and 36 amino acid residues (i.e., peptides ranging in size from a tripeptide to a 36-mer polypeptide), and may include but are not limited to those listed in Tables I and II, below. Peptide sequences in these tables are listed from amino (left) to carboxy (right) terminus. "X" may represent an amino group (—NH$_2$) and "Z" may represent a carboxyl (—COOH) group. Alternatively, as described below, "X" and/or "Z" may represent a hydrophobic group, an acetyl group, a FMOC group, an amido group, or a covalently attached macromolecule.

DP-107 is a 38 amino acid peptide corresponding to residues 558 to 595 of HIV-1$_{LA1}$ transmembrane (TM) gp41 protein, which exhibits potent antiviral activity. DP-107 is an HIV-1-derived antiviral peptide and may also be found in other, non-HIV-1 envelope viruses. DP-107 is more fully described in Applicant's co-pending U.S. patent applications Ser. No. 08/470,896, filed Jun. 6, 1995, Ser. No. 08/374,666, filed Jan. 27, 1995, Ser. No. 08/264,531, filed Jun. 23, 1994, and Ser. No. 08/255,208, filed Jun. 7, 1994, which are incorporated herein by reference in their entirety.

Deletions of DP107 or DP178 truncations are also within the scope of the invention. Such deletions consist of the removal of one or more amino acids from the DP107 or DP707-like peptide sequence, with the lower limit length of the resulting peptide sequence being 4 to 6 amino acids. Such deletions may involve a single contiguous or greater than one discrete portion of the peptide sequences. One or more such deletions may be introduced into DP107 or DP107 truncations, as such deletions result in peptides which may still be recognized by the 107×78×4, ALLMOTI5 or PLZIP search motifs described herein, or may, alternatively, exhibit antifusogenic or antiviral activity, or exhibit the ability to modulate intracellular processes involving coiled-coil peptide structures.

DP107 and DP107 truncations are more fully described in Applicants' co-pending U.S. patent application Ser. No. 08/374,666, filed Jan. 27, 1995, and which is incorporated herein by reference in its entirety.

TABLE I

| DP-178 (SEQ ID: 1) CARBOXY TRUNCATIONS |
| --- |
| X-YTS-Z |
| X-YTSL-Z |
| X-YTSLI-Z |
| X-YTSLIH-Z |
| X-YTSLIHS-Z |
| X-YTSLIHSL-Z |
| X-YTSLIHSLI-Z |
| X-YTSLIHSLIE-Z |
| X-YTSLIHSLIEE-Z |
| X-YTSLIHSLIEES-Z |
| X-YTSLIHSLIEESQ-Z |
| X-YTSLIHSLIEESQN-Z |
| X-YTSLIHSLIEESQNQ-Z |
| X-YTSLIHSLIEESQNQQ-Z |
| X-YTSLIHSLIEESQNQQE-Z |
| X-YTSLIHSLIEESQNQQEK-Z |
| X-YTSLIHSLIEESQNQQEKN-Z |

TABLE I-continued

DP-178 (SEQ ID: 1) CARBOXY TRUNCATIONS

X-YTSLIHSLIEESQNQQEKNE-Z
X-YTSLIHSLIEESQNQQEKNEQ-Z
X-YTSLIHSLIEESQNQQEKNEQE-Z
X-YTSLIHSLIEESQNQQEKNEQEL-Z
X-YTSLIHSLIEESQNQQEKNEQELL-Z
X-YTSLIHSLIEESQNQQEKNEQELLE-Z
X-YTSLIHSLIEESQNQQEKNEQELLEL-Z
X-YTSLIHSLIEESQNQQEKNEQELLELD-Z
X-YTSLIHSLIEESQNQQEKNEQELLELDK-Z
X-YTSLIHSLIEESQNQQEKNEQELLELDKW-Z
X-YTSLIHSLIEESQNQQEKNEQELLELDKWA-Z
X-YTSLIHSLIEESQNQQEKNEQELLELDKWAS-Z
X-YTSLIHSLIEESQNQQEKNEQELLELDKWASL-Z
X-YTSLIHSLIEESQNQQEKNEQELLELDKWASLW-Z
X-YTSLIHSLIEESQNQQEKNEQELLELDKWASLWN-Z
X-YTSLIHSLIEESQNQQEKNEQELLELDKWASLWNW-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxycarbonyl (FMOC) group; a macromolecular carrier group including but not limited to lipid-fatty acid conjugates, polyethylene glycol, or carbohydrates.
"Z" may represent a carboxyl group; an amido group; a T-butyloxycarbonyl group; a macromolecular carrier group including but not limited to lipid-fatty acid conjugates, polyethylene glycol, or carbohydrates.

TABLE II

DP-178 (SEQ ID: 1) AMINO TRUNCATIONS

X-NWF-Z
X-WNWF-Z
X-LWNWF-Z
X-SLWNWF-Z
X-ASLWNWF-Z
X-WASLWNWF-Z
X-KWASLWNWF-Z
X-DKWASLWNWF-Z
X-LDKWASLWNWF-Z
X-ELDKWASLWNWF-Z
X-LELDKWASLWNWF-Z
X-LLELDKWASLWNWF-Z
X-ELLELDKWASLWNWF-Z
X-QELLELDKWASLWNWF-Z
X-EQELLELDKWASLWNWF-Z
X-NEQELLELDKWASLWNWF-Z
X-KNEQELLELDKWASLWNWF-Z
X-EKNEQELLELDKWASLWNWF-Z
X-QEKNEQELLELDKWASLWNWF-Z
X-QQEKNEQELLELDKWASLWNWF-Z
X-NQQEKNEQELLELDKWASLWNWF-Z
X-QNQQEKNEQELLELDKWASLWNWF-Z
X-SQNQQEKNEQELLELDKWASLWNWF-Z
X-ESQNQQEKNEQELLELDKWASLWNWF-Z
X-EESQNQQEKNEQELLELDKWASLWNWF-Z
X-IEESQNQQEKNEQELLELDKWASLWNWF-Z
X-LIEESQNQQEKNEQELLELDKWASLWNWF-Z
X-SLIEESQNQQEKNEQELLELDKWASLWNWF-Z
X-HSLIEESQNQQEKNEQELLELDKWASLWNWF-Z
X-IHSLIEESQNQQEKNEQELLELDKWASLWNWF-Z
X-LIHSLIEESQNQQEKNEQELLELDKWASLWNWF-Z
X-SLIHSLIEESQNQQEKNEQELLELDKWASLWNWF-Z
X-TSLIHSLIEESQNQQEKNEQELLELDKWASLWNWF-Z
X-YTSLIHSLIEESQNQQEKNEQELLELDKWASLWNWF-Z

The one letter amino acid code is used.
Additionally,
"X" may represent an amino group, a hydrophobic group, including but not limited to carbobenzoxyl, dansyl, or T-butyloxycarbonyl; an acetyl group; a 9-fluorenylmethoxycarbonyl group; a macromolecular carrier group including but not limited to lipid-fatty acid conjugates, polyethylene glycol, or carbohydrates.

"Z" may represent a carboxyl group; an amido group; a T-butyloxycarbonyl group; a macromolecular carrier group including but not limited to lipid-fatty acid conjugates, polyethylene glycol, or carbohydrates.

5.1.2. DP-178 and DP-107 Analogs and Homologs

The antiviral peptides of the invention also include analogs of DP-178 and/or DP-178 truncations which may include, but are not limited to, peptides comprising the DP-178 (SEQ ID:1) sequence, or DP-178 truncated sequence, containing one or more amino acid substitutions, insertions and/or deletions. Analogs of DP-178 homologs, described below, are also within the scope of the invention. The DP-178 analogs of the invention exhibit antiviral activity, and may, further, possess additional advantageous features, such as, for example, increased bioavailability, and/or stability, or reduced host immune recognition.

HIV-1 and HIV-2 envelope proteins are structurally distinct, but there exists a striking amino acid conservation within the DP-178-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP-178 peptides of the invention.

Amino acid substitutions may be of a conserved or non-conserved nature. Conserved amino acid substitutions consist of replacing one or more amino acids of the DP-178 (SEQ ID:1) peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to DP-178 (SEQ ID:1) or the DP-178 peptide from which it is derived. Non-conserved substitutions consist of replacing one or more amino acids of the DP-178 (SEQ ID:1) peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues ranging from 2 to 15 amino acids in length. One or more insertions may be introduced into DP-178 (SEQ ID:1), DP-178 fragments, analogs and/or DP-178 homologs.

Deletions of DP-178 (SEQ ID:1), DP-178 fragments, analogs, and/or DP-178 homologs are also within the scope of the invention. Such deletions consist of the removal of one or more amino acids from the DP-178 or DP-178-like peptide sequence, with the lower limit length of the resulting peptide sequence being 4 to 6 amino acids. Such deletions may involve a single contiguous or greater than one discrete portion of the peptide sequences.

The peptides of the invention may further include homologs of DP-178 (SEQ ID:1) and/or DP-178 truncations which exhibit antiviral activity. Such DP-178 homologs are peptides whose amino acid sequences are comprised of the amino acid sequences of peptide regions of other (i.e., other than HIV-1$_{LA1}$) viruses that correspond to the gp41 peptide region from which DP-178 (SEQ ID:1) was derived. Such viruses may include, but are not limited to, other HIV-1 isolates and HIV-2 isolates. DP-178 homologs derived from the corresponding gp41 peptide region of other (i.e., non HIV-1$_{LAI}$) HIV-1 isolates may include, for example, peptide sequences as shown below.

NH$_2$-YT<u>NTI</u>YTL
LEESQNQQEKNEQELLELDKWASLWNWF-COOH
(DP-185; SEQ ID:3);

NH$_2$-YT<u>GII</u>YNL
LEESQNQQEKNEQELLELDKWA<u>N</u>LWNWF-COOH
(SEQ ID:4);

NH$_2$-YTSL<u>I</u>YSL<u>L</u>E
<u>K</u>SQIQQEKNEQELLELDKWASLWNWF-COOH
(SEQ ID:5).

SEQ ID:3 (DP-185), SEQ ID:4, and SEQ ID:5 are derived from HIV-1$_{SF2}$, HIV-1$_{RF}$, and HIV-1$_{MN}$ isolates, respectively. Underlined amino acid residues refer to those residues that differ from the corresponding position in the DP-178 (SEQ ID:1) peptide. One such DP-178 homolog, DP-185 (SEQ ID:3), is described in the Working Example presented in Section 6, below, where it is demonstrated that DP-185 (SEQ ID:3) exhibits antiviral activity. The DP-178 homologs of the invention may also include truncations, amino acid substitutions, insertions, and/or deletions, as described above.

In addition, striking similarities, as shown in FIG. 1, exist within the regions of HIV-1 and HIV-2 isolates which correspond to the DP-178 sequence. A DP-178 homolog derived from the HIV-2$_{NIHZ}$ isolate has the 36 amino acid sequence (reading from amino to carboxy terminus):

NH$_2$-LEANISQSLEQAQIQQEKNMYELQKLNSWD
VFTNWL-COOH (SEQ ID:7)

Table III and Table IV show some possible truncations of the HIV-2$_{NIHZ}$ DP-178 homolog, which may comprise peptides of between 3 and 36 amino acid residues (i.e., peptides ranging in size from a tripeptide to a 36-mer polypeptide). Peptide sequences in these tables are listed from amino (left) to carboxy (right) terminus. "X" may represent an amino group (—NH$_2$) and "Z" may represent a carboxyl (—COOH) group. Alternatively, as described below, "X" and/or "Z" may represent a hydrophobic group, an acetyl group, a FMOC group, an amido group, or a covalently attached macromolecule, as described below.

TABLE IV

HIV-2$_{NIHZ}$ DP-178 homolog amino truncations.

X-NWL-Z
X-TNWL-Z
X-FTNWL-Z
X-VFTNWL-Z
X-DVFTNWL-Z
X-WDVFTNWL-Z
X-SWDVFTNWL-Z
X-NSWDVFTNWL-Z
X-LNSWDVFTNWL-Z
X-KLNSWDVFTNWL-Z
X-QKLNSWDVFTNWL-Z
X-LQKLNSWDVFTNWL-Z
X-ELQKLNSWDVFTNWL-Z
X-YELQKLNSWDVFTNWL-Z
X-MYELQKLNSWDVFTNWL-Z
X-NMYELQKLNSWDVFTNWL-Z
X-KNMYELQKLNSWDVFTNWL-Z
X-EKNMYELQKLNSWDVFTNWL-Z
X-QEKNMYELQKLNSWDVFTNWL-Z
X-QQEKNMYELQKLNSWDVFTNWL-Z
X-IQQEKNMYELQKLNSWDVFTNWL-Z
X-QIQQEKNMYELQKLNSWDVFTNWL-Z
X-AQIQQEKNMYELQKLNSWDVFTNWL-Z
X-QAQIQQEKNMYELQKLNSWDVFTNWL-Z
X-EQAQIQQEKNMYELQKLNSWDVFTNWL-Z
X-LEQAQIQQEKNMYELQKLNSWDVFTNWL-Z
X-SLEQAQIQQEKNMYELQKLNSWDVFTNWL-Z
X-QSLEQAQIQQEKNMYELQKLNSWDVFTNWL-Z
X-SQSLEQAQIQQEKNMYELQKLNSWDVFTNWL-Z
X-ISQSLEQAQIQQEKNMYELQKLNSWDVFTNWL-Z
X-NISQSLEQAQIQQEKNMYELQKLNSWDVFTNWL-Z
X-ANISQSLEQAQIQQEKNMYELQKLNSWDVFTNWL-Z
X-EANISQSLEQAQIQQEKNMYELQKLNSWDVFTNWL-Z
X-LEANISQSLEQAQIQQEKNMYELQKLNSWDVFTNWL-Z

The one letter amino acid code is used.

Additionally,

"X" may represent an amino group, a hydrophobic group, including but not limited to carbobenzoxyl, dansyl, or T-butyloxycarbonyl; an acetyl group; a 9-fluorenylmethoxy-carbonyl (FMOC) group; a macromolecular carrier group including but not limited to lipid-fatty acid conjugates, polyethylene glycol, or carbohydrates.

TABLE 3

Combination Indices from in vitro HIV-1IIIb/CEM Co-culture

| Combinations | Ratio by weight | Relationship | CI ED50 | ED75 | ED90 | ED95 | r | Dm ng/ml T20 | Drug #2 |
|---|---|---|---|---|---|---|---|---|---|
| T:20:AZT | 1:10 | +++ | 0.50 | 0.43 | 0.38 | 0.38 | 0.94 | 298.50 | 13137.00 |
| T20:3TC | 1:1.5 | +/− | 1.38 | 1.16 | 0.99 | 0.88 | 0.99 | 158.87 | 74.76 |
|  | 2:1 | ++ | 0.86 | 0.82 | 0.78 | 0.75 | 0.97 | 298.50 | 63.73 |
| T20:Indinavir | 10:1 | +++ | 0.61 | 0.48 | 0.37 | 0.31 | 0.99 | 298.50 | 27.60 |
| T20:Nelfinavir | 1.33:1 | ++ | 1.04 | 0.78 | 0.62 | 0.50 | 0.93 | 172.02 | 9.27 |
|  | 5:1 | +++ | 0.64 | 0.57 | 0.51 | 0.51 | 0.95 | 298.50 | 60.88 |

Control Combinations

| Combinations | Ratio by wt. | Relationship | CI ED50 | ED75 | ED90 |
|---|---|---|---|---|---|
| AZT/3TC | 20:1 | ++++ | 0.20 | 0.29 | 0.42 |
| AZT/IDV | 100:1 | +++ | 0.24 | 0.25 | 0.26 |
| IDV/3TC | 1:5 | + | 0.82 | 0.86 | 0.91 |
| T20/T20 | 1:1 | − | 1.25 | 1.20 | 1.15 |

"Z" may represent a carboxyl group; an amido group; a T-butyloxycarbonyl group; a macromolecular carrier group including but not limited to lipid-fatty acid conjugates, polyethylene glycol, or carbohydrates.

5.1.3. Preparation of DP-178 and DP-107

The peptides of the invention may be synthesized or prepared by techniques well known in the art. See, for example, Creighton, 1983, Proteins: Structures and Molecular Principles, W. H. Freeman and Co., NY, which is incorporated herein by reference in its entirety. Short peptides, for example, can be synthesized on a solid support or in solution. Longer peptides amy be made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, NY.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. (See "X" in Tables I to IV, above.) Additionally, the hydrophobic group, t-butyloxycarbonyl, or an amido group may be added to the peptides' carboxy termini. (See "Z" in Tables I to IV, above.) Further, the peptides of the invention may be synthesized such that their steric configuration is altered. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or inhibitory action of the peptides of the invention.

Any of the peptides described above may, additionally, have a non-peptide macromolecular carrier group covalently attached to their amino and/or carboxy termini. Such macromolecular carrier groups may include, for example, lipid-fatty acid conjugates, polyethylene glycol, or carbohydrates. The truncations, analogs and homologs of DP-178 and DP-107 are described fully in Applicant's co-pending applications Ser. No. 08/073,028, filed Jun. 7, 1993, Ser. No. 08/264,531, filed Jun. 23, 1994, Ser. No. 08/255,208, filed Jun. 7, 1994 and Ser. No. 08/360,107, filed Dec. 20, 1994, which are incorporated herein by reference in their entirety.

5.1.4. Therapeutic Uses of the Peptides of the Invention

The DP-178 (SEQ ID:1) peptides of the invention, and DP-178 fragments, analogs, and homologs, exhibit potent antiviral activity. The DP-107-like and DP-178-like peptides of the invention preferably exhibit antiviral activity. As such, the peptides may be used as inhibitors of human and non-human viral and retroviral, especially HIV, transmission to uninfected cells.

The human retroviruses whose transmission may be inhibited by the peptides of the invention include, but are not limited to all strains of HIV-1 and HIV-2 and the human T-lymphocyte viruses (HTLV-I and II). The non-human retroviruses whose transmission may be inhibited by the peptides of the invention include, but are not limited to bovine leukosis virus, feline sarcoma and leukemia viruses, simian immunodeficiency, sarcoma and leukemia viruses, and sheep progress pneumonia viruses.

Non retroviral viruses whose transmission may be inhibited by the peptides of the invention include, but are not limited to human respiratory syncytial virus, canine distemper virus, newcastle disease virus, human parainfluenza virus, and influenza viruses.

The invention further encompasses the treatment of the above retroviral and non-retroviral viruses using the peptides in combination therapy.

5.2. Antivirals to be Used in Combination with DP-178 or DP-107

According to the present invention, DP-178 or DP-107, a virus fusion inhibitor, may be used in combination with other therapeutic agents to enhance its antiviral effect achieved. Preferably DP-178 or DP-107 is used in combination with another antiviral agent. Such additional antiviral agents which may be used with DP-178 or DP-107 include but are not limited to those which function on a different target molecule involved in viral replication, e.g., reverse transcriptase inhibitors, viral protease inhibitors, glycosylation inhibitors; those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity.

DP-178 or DP-107 or a pharmaceutically acceptable derivative thereof can also be used in combination with retrovirus inhibitors, such as nucleoside derivatives. Nucleoside derivatives are modified forms of purine and pyrimidine nucleosides which are the building blocks of RNA and DNA. Many of the nucleoside derivatives under study as potential anti-HIV medications result in premature termination of viral DNA replication before the entire genome has been transcribed. These derivatives lack 3' substituents that can bind to subsequent nucleosides and result in chain termination. Nucleoside derivatives such as 3'azido-3'-thymidine (AZT) and dideoxyinosine (ddI) have been exploited as inhibitors of HIV-1 replication, both in vitro and in vivo. Nucleoside analogs are the currently the only licensed therapeutics for the treatment of HIV infection and AIDS (Fischl et al, 1987 N. Engl. J. Med. 317, 185–191; Mitsuya and Broder, 1987 Nature 325, 773–778). This class of compounds works by inhibiting reverse transcriptase resulting in a block in cDNA synthesis (Mitsuya and Broder, 1987), these inhibitors work early in the infectious cycle of HIV-1 and inhibit integration into T-cell genome. However, AZT therapy leads to development of resistant HIV strains (Larder 1989, 1991, Ibid.) and demonstrates toxicity in AIDS patients upon long-term therapy (Fischl et al., 1987, N. Engl. J. Med. 317:185–191; Creagh-Kirk, et al., 1988, J.A.M.A. 15 260:3045–3048).

Further, DP-178 or DP-107 or a pharmaceutically acceptable derivative thereof can be used in combination with nucleoside derivatives which include but are not limited to, 2',3'-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxydideoxythymidine (d4T) and 3'-azido-2',3'-dideoxythymidine (AZT). Alternatively, halogenated nucleoside derivatives may be used, preferably 2',3'-dideoxy-2'-fluoronucleosides including, but not limited to, 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T). Preferably, the 2',3'-dideoxy-2'-fluoronucleosides of the invention are those in which the fluorine linkage is in the beta configuration, including, but not limited to, 2'3'-dideoxy-2'-beta-fluoroadenosine (F-ddA), 2',3'-dideoxy-2'-beta-fluoroinosine (F-ddI), and 2',3'-dideoxy-2'-beta-fluorocytosine (F-ddC). Such combinations allow one to use a lower dose of the nucleoside derivative thus reducing the toxicity associated with that agent, without loss of antiviral activity because of the use of the antiviral peptides. Moreover, such a combination reduces or avoids viral resistance.

Preferred combinations of antiviral peptides and nucleoside derivatives within the scope of the present invention include an effective amount of DP-107, DP-178 or a pharmaceutically acceptable derivative thereof and an effective amount of AZT to treat HIV infection; and an effective amount of DP-107, DP-178 or a pharmaceutically acceptable derivative thereof and an effective amount of ddI.

According to the present invention, DP-178 or DP-107 or a pharmaceutically acceptable derivative thereof can also be used in combination with uridine phosphorylase inhibitors, including but not limited to acyclouridine compounds, including benzylacyclouridine (BAU); benzyloxybenzylacyclouridine (BBAU); aminomethyl-benzylacyclouridine (AM BAU); aminomethyl-benzyloxybenzylacyclouridine (AMB-BAU); hydroxymethyl-benzylacyclouridine (HMBAU); and hydroxymethyl-benzyloxybenzylacyclouridine (HMBBAU).

According to the present invention, DP-178 or DP-107 or a pharmaceutically acceptable derivative thereof can also be used in combination with cytokines or cytokine inhibitors, including but not limited to rIFN α, rIFN β, rIFN γ, inhibitors of TNFα, and MNX-160. Human rIFN-αA (>108 IU/mg) and rIFN γ (1.4×108 IU/mg) can be obtained from Hoffman LaRoche. Human rIFN β Ser 17 (1.0×108 IU/mg) are obtained from Triton Biosciences. Reference standards are obtained from the World Health Organization (human IFNα WHO standard B,69,19 and human IFN β, WHO no. G-023-902-527, or the National Institute of Allergy and Infectious Disease (human γ, National Institute of Health no. G-023-901-530.

According to the present invention, DP-178 or DP-107 or a pharmaceutically acceptable derivative thereof can be used in combination with viral protease inhibitors, including but not limited to, MK-639 (Merck), Invirase (saquinavir, Roche), ABT-538 (Abbott, CAS Reg. No. 155213-67-5), AG1343, VX0478 (Burroughs Wellcome/Glaxo, CAS Reg. No. 161814-49-9), DMP450, SC-52151 (Telinavir). Protease inhibitors are generally thought to work primarily during or after assembly (i.e., viral budding) to inhibit maturation of virions to a mature infectious state. For example, ABT-538 has been shown to have potent antiviral activity in vitro and favorable pharmokinetic and safety profiles in vivo (Ho, et al., 1995, Nature 373: 123–126). Administration of ABT-538 to AIDS patients causes plasma HIV-1 levels to decrease exponentially and CD4 lymphocyte counts to rise substantially. The exponential decline in plasma viraemia following ABT-538 treatment reflects both the clearance of free virions and the loss of HIV-1 producing cells as the drug substantially blocks new rounds of infection. ABT-538 treatment reduces virus-mediated destruction of CD4 lymphocytes. Combining this treatment with DP-178 and/or DP-107, which inhibits at an earlier stage of HIV infection, viral fusion, would be likely to have synergistic effects and have a dramatic clinical impact.

DP-178 or DP-107 or a pharmaceutically acceptable derivative thereof can also be used in combination with a class of anti-HIV drugs which interfere with 5'-mRNA processing, for example ribavirin. (Ribavirin (Virazole) from Viratel Inc.). Although the mechanism of action of ribavirin is not clear, this drug is thought to compete with guanosine in the formation of mRNA cap structures and/or interfere with the functional methylation of these molecules. These viruses which may escape the inhibition of viral fusion by DP-178 and/or DP-107 would be blocked by ribavirin and thereby exhibiting synergy of the anti-HIV mechanism of DP-178 and/or DP-107 and ribavirin.

In addition, DP-178, DP-107 or a pharmaceutically acceptable derivative thereof can be used in combination with therapeutic agents, such as Amphotericin B (Fungizone, obtained from Gibco) a polyene microlide antifungal antibiotic which interacts with sterols and binds to them irreversibly. Amphotericin B represents a unique class of agents that are active against a variety of lipid-enveloped viruses, including HIV. Although amphotericin exhibits severe in vivo toxicities, the methyl ester form of this drug also exhibits anti-HIV activity and has a low cellular toxicity profile in vitro. Therefore amphotericin B or its methyl ester can be used in combinational therapy with DP-178, DP-107 or a pharmaceutical derivative thereof. This combination allows the clinician to employ a lower i.e. less toxic dose of ether Amphotericin B or its methyl ester without concern for loss of antiviral activity since it is used in conjunction with the antiviral peptides DP-178 or DP-107.

According to the present invention, DP-178 or DP-107 or a pharmaceutically acceptable derivative thereof can also be used in combination with inhibitors of glycoprotein processing, such as castonospermine (Boehringer Mannheim). Castanospermine is a plant alkaloid which inhibits glycoprotein processing, and acts as an anti-HIV since HIV contains two heavily glycosylated proteins, gp120 and gp41. Protein glycosylation plays an important role in gp120 interaction with CD4. Under conditions of infection by progeny virions synthesized in the presence of castanospermine the infectivity of HIV was attenuated. Therefore it is likely that DP-178, DP-107 or a pharmaceutically acceptable derivative thereof in combination with castanospermine would act synergistically to inhibit viral entry and hence attenuate infection.

Preferred combinations to be used within the methods of treating HIV include the use of an effective amount of DP-107, DP-178 or a pharmaceutically acceptable derivative thereof and an effective amount of ddI; the use of an effective amount of DP-107, DP-178 or a pharmaceutically acceptable derivative thereof and an effective amount of 3TC; and the use of an effective amount of DP-107, DP-178 or a pharmaceutically acceptable derivative thereof and an effective amount ribavirin.

A further preferred combinations to be used within the methods of treating HIV include the use of an effective amount of DP-107, DP-178 or a pharmaceutically acceptable derivative thereof and an effective amount of beta-interferon.

Yet another combination to be used with the methods of treating HIV include the use of an effective amount of DP-107, DP-178 or a pharmaceutically acceptable derivative thereof and an effective amount of protease inhibitors.

In order to evaluate potential therapeutic efficacy of DP-178, DP-107 or a pharmaceutically acceptable derivative thereof in combination with the antiviral therapeutics described above, these combinations may be tested for antiviral activity according to methods known in the art. For example, the ability of a DP-178 and AZT combination to inhibit HIV cytotoxicity, syncytia formation, reverse transcriptase activity, or generation of viral RNA or proteins may be tested in vitro, as described in Example 6.

5.2.1. Therapeutic Uses of HIV-Inhibitory Combinations

The improved or synergistic DP-178 or DP-107 combination therapy as described above may be used in accordance with the invention in vivo to prevent the formation of syncytia and the production of HIV virions and, thus, inhibit the progression of HIV within an exposed patient. The combinational therapy of the present invention is also useful to alleviate or treat disease associated with HIV-infected immunosuppressed patients. For example, the antiviral peptides DP-178, DP-107 or pharmaceutically acceptable derivatives thereof may be used in combination with antifungal agents, antivirals effects against HBV, EBV, CMV, and other opportunistic infections including TB.

The antiviral peptide of the present invention, DP-178, DP-107 or pharmaceutically acceptable derivatives thereof are preferably used against HIV infection. Effective doses of the combination therapy as described below may be formulated in suitable pharmacological carriers and may be administered by any appropriate means including but not limited to injection (e.g., intravenous, intraperitoneal, intramuscular, subcutaneous, etc.), by absorption through epithelial or mucocutaneous linings (e.g., oral mucosa, rectal and vaginal epithelial linings, nasopharyngeal mucosa, intestinal mucosa, etc.); orally, transdermally or any other means available within the pharmaceutical arts.

5.3. Pharmaceutical Formulations, Dosages and Modes of Administration 5.3.1. Pharmaceutical Compositions The pharmaceutical compositions of the invention which are useful in the treatment or prevention of viral infections in humans contain as an active agent DP-178, DP-107 or a pharmaceutically acceptable derivative thereof, and at least one other therapeutic agent, such as another antiviral. The pharmaceutical compositions of the present invention provide combinational therapy that may have either additive and/or synergistic effects.

Preferably, the pharmaceutical compositions containing DP-178 or DP-107 or a pharmaceutically acceptable derivative thereof also contain at least one other antiviral agent, such as reverse transcriptase inhibitors, protease inhibitor, inhibitors of mRNA processing, inhibitors of protein glycosylation and inhibitors of viral fusion. Such agents include but are not limited to nucleoside analogs or chain terminators (e.g., dideoxynucleosides).

Additional suitable therapeutic agents which may be used in combinational therapy with DP-178 or DP-107 or a pharmaceutically acceptable derivative thereof within the scope of the invention include but are not limited to 2-deoxy-D-glucose (2-dGlc), deoxynojirimycin, acycloguanosine, ribavirin (virazole), rifampicin (rifadin), adamantidine, rifabutine, ganciclover, (DHPG), fluoroiodoaracytosine, idoxurine, trifluorothymidine, adenine arabinoside (ara-A), ara-AMP, bromovinyldeoxyuridine, bromovinylarauracil (BV-araU by Bristol-Meyers Squibb (1-beta-D-arabinofuranoside-E-5-[2-bromovinyl] uracil)) rimantadine, arildone, diarylamidine, (S)-(p-nitrobenzyl-)6-thioinosine and phosphonoformate.

Novel pharmaceutical compositions encompassed by the present invention include but are not limited to DP-178, DP-107 or a pharmaceutically acceptable derivative, and rifampicin (rifadin); DP-178 or DP-107 and AZT; DP-178 or DP-107 and ddI; DP-178 or DP-107 and ddC; DP-178 or DP-107 and adamantidine; DP-178 or DP-107 and acycloguanosine; DP-178 or DP-107 and 2-deoxy-D-glucose; DP-178 or DP-107 and deoxynojirimycin; DP-178 or DP-107 and interferon-$\alpha$ and DP-178 or DP-107 and ganciclovir. The present invention also encompasses pharmaceutical compositions which contain DP-178 or DP-107, or a pharmaceutically acceptable derivative, and optionally more than one additional therapeutic compound.

The peptides of the invention may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Most preferably, administration is intravenous. For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In addition, the peptides may be used as a prophylactic measure in previously uninfected individuals after acute exposure to an HIV virus. Examples of such prophylactic use of the peptides may include, but are not limited to, prevention of virus transmission from mother to infant and other settings where the likelihood of HIV transmission exists, such as, for example, accidents in health care settings wherein workers are exposed to HIV-containing blood products. The peptides of the invention in such cases may serve the role of a prophylactic vaccine, wherein the host raises antibodies against the peptides of the invention, which then serve to neutralize HIV viruses by, for example, inhibiting further HIV infection. Administration of the peptides of the invention as a prophylactic vaccine, therefore, would comprise administering to a host a concentration of peptides effective in raising an immune response which is sufficient to neutralize HIV, by, for example, inhibiting HIV ability to infect cells. The exact concentration will depend upon the specific peptide to be administered, but may be determined by using standard techniques for assaying the development of an immune response which are well known to those of ordinary skill in the art. The peptides to be used as vaccines are usually administered intramuscularly.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

Effective dosages of the peptides of the invention to be administered may be determined through procedures well known to those in the art which address such parameters as biological half-life, bioavailability, and toxicity. Given the data presented below in Section 6, DP-178, for example, may prove efficacious in vivo at doses required achieve circulating levels of 10 ng per ml of peptide.

5.3.2. Dosage

In treating mammals, including humans, having a viral infection a therapeutically effective amount of DP-178, DP-107 or a pharmaceutically acceptable derivative is administered, i.e., a dose sufficient to inhibit viral replication. For example DP-178 or DP-107 may be administered as an infusion at about 0.1 mg/kg to 1.0 mg/kg per day for about 12 weeks. A preferable dose is from 20 mg to 35 mg; the equivalent daily dose of DP-178 or DP-107 or a pharmaceutically acceptable derivative thereof based on surface area is from about 7 mg to 70 mg. The most preferred dose is about 20 mg to 35 mg for about 12 weeks. Doses of DP-178, DP-107 or a pharmaceutically acceptable derivative should be administered in intervals of from about once per day to 4 times per day and preferably from about once every two days to once per day. A preferred dose is administered to achieve peak plasma concentrations of DP-178, DP-107 or a pharmaceutically acceptable derivative thereof from about 1 mg/ml to 10 mg/ml. This may be achieved by the sterile injection of a 2.0% solution of the administered ingredients in buffered saline (any suitable saline solutions known to those skilled in the art of chemistry may be used). Desirable blood levels may be maintained by a continuous infusion of DP-178 or DP-107 as ascertained by plasma levels measured by HPLC.

Effective amounts of the therapeutic agents, e.g., antivirals to be used in combination with DP-178, DP-107 or a pharmaceutically acceptable derivative thereof are based on the recommended doses known to those skilled in the art for the various antivirals. For example, doses for AZT, ddI and interferon-Beta can be found in standard physician reference texts. In addition, doses for other therapeutic agents, including antivirals, are reported in the literature, for example, ABT-538 is administered orally 600–1,200 mg/day on day 1 and daily thereafter (Ho, et al., 1995, Nature 373: 123–126). These recommended or known levels will preferably be lowered by 10% to 50% of the cited dosage after testing the effectiveness of these dosages in combination with DP-178, DP-107 or a pharmaceutically acceptable derivative, using the assays described in Section 5.4 infra. It should be noted that the attending physician would know how to and when to terminate, interrupt, or adjust therapy to lower dosage due to toxicity, bone marrow, liver or kidney dysfunctions or adverse drug-drug interaction. Conversely, the attending physician would also know to adjust treatment to higher levels if the clinical response is not adequate (precluding toxicity).

A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of RT production from infected cells compared to untreated control as determined in cell culture. Such information can be used to more accurately determine useful doses in humans. Levels in plasma may be measured, for example, by high performance liquid chromatography (HPLC).

5.4. Pharmaceutical Formulations and Routes of Administration

Pharmaceutical compositions containing DP-178, DP-107 or a pharmaceutically acceptable derivative can be administered to a human patient, by itself, or in pharmaceutical compositions where it is mixed with suitable carriers or excipient(s) at doses to treat a viral infection, in particular HIV infection. Techniques for formulation and administration of the compounds of the instant application may be found in "Remington's Pharmaceutical Sciences," Mack Publishing Co., Easton, Pa., latest edition.

As demonstrated in the Example presented below in Section 6, the antiviral activity of the peptides of the invention may show a pronounced type and subtype specificity, i.e., specific peptides may be effective in inhibiting the activity of only specific viruses. This feature of the invention presents many advantages. One such advantage, for example, lies in the field of diagnostics, wherein one can use the antiviral specificity of the peptide of the invention to ascertain the identity of a viral isolate. With respect to HIV, one may easily determine whether a viral isolate consists of an HIV-1 or HIV-2 strain. For example, uninfected CD-4$^+$ cells may be co-infected with an isolate which has been identified as containing HIV the DP-178 (SEQ ID:1) peptide, after which the retroviral activity of cell supernatants may be assayed, using, for example, the techniques described above in Section 5.2. Those isolates whose retroviral activity is completely or nearly completely inhibited contain HIV-1. Those isolates whose viral activity is unchanged or only reduced by a small amount, may be considered to not contain HIV-1. Such an isolate may then be treated with one or more of the other DP-178 peptides of the invention, and subsequently be tested for its viral activity in order to determine the identify of the viral isolate.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. Dosage forms include but are not limited to tablets, troches, dispersions, suspensions, suppositories, solutions, capsules, creams, patches, minipumps and the like.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

5.5. Assays For Antiviral Activity

The antiviral activity exhibited by the combination therapy of the invention may be measured, for example, by easily performed in vitro assays, such as those described below, which can test the peptides' ability to inhibit syncytia formation, or their ability to inhibit infection by cell-free virus. Using these assays, such parameters as the relative antiviral activity of the peptides, exhibit against a given strain of virus and/or the strain specific inhibitory activity of the peptide can be determined. A cell fusion assay may be utilized to test the peptides' ability to inhibit HIV-induced syncytia formation in vitro. Such an assay may comprise culturing uninfected CD-4$^+$ cells (such as Molt or CEM cells, for example) in the presence of chronically HIV-infected cells and a therapeutic agent to be assayed. For each combinational therapy, a range of concentrations may be tested. This range should include a control culture wherein no peptide has been added. Standard conditions for culturing, well known to those of ordinary skill in the art, are used. After incubation for an appropriate period (24 hours at 37° C., for example) the culture is examined microscopically for the presence of multinucleated giant cells, which are indicative of cell fusion and syncytia formation.

A reverse transcriptase (RT) assay may be utilized to test the peptides' ability to inhibit infection of CD-4$^+$ cells by cell-free HIV in combination with another antiviral agent. Such an assay may comprise culturing an appropriate concentration (i.e., TCID$_{50}$) of virus and CD-4$^+$ cells in the presence of the peptide and the antiviral in combination to be tested. Culture conditions well known to those in the art are used. As above, a range of peptide concentrations may be used, in addition to a control culture wherein no peptide has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, J. Virol. 38:239–248) and/or Willey et al. (Willey, R. et al., 1988, J. Virol. 62:139–147). These references are incorporated herein by reference in their entirety.

Standard methods which are well-known to those of skill in the art may be utilized for assaying non-retroviral activity. See, for example, Pringle et al. (Pringle, C. R. et al., 1985, J. Medical Virology 17:377–386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in its entirety.

5.5.1. Testing of Antiviral Compounds Active at Different Stages of HIV-1 Infection Three separate in vitro assays for the study of antiviral compounds active at different stages of HIV infection (acute, co-cultivation, and chronic) are well known to those skilled in the art (Lambert et al., 1993, Antiviral Res. 21: 327–342). These assays can be used to assess the effects of DP-178, DP-107 or a pharmaceutically acceptable derivative thereof in combination with one of the described antiviral agents. All assays are carried out in triplicate in 24-well plates (Nunc.) 5-fold serial dilutions of inhibitor are made in 100% DMSO to yield 200×final concentrations. Addition of ½₀₀ vol. of dilutions to culture wells resulted in a final concentration of 0.5% DMSO and the desired concentration of the inhibitor. Experiments are carried out either with dilutions of fixed ratio of the two inhibitors (i.e., 1:10 or 1:40, AZT:DP-178) or where the concentrations are varied.

First the acute infection assay models the rapid replication and cytopathic effects contributing to the loss of CD-4+ cells in vivo. Assay the treatment of acutely infected Molt4 cells to show the antiviral compounds are effective at inhibiting the spread of HIV-1 infection in T cells. For these assays, 3×10$^4$ uninfected Molt4 cells per well are infected with 50 TCIDs of HIV-1 (strain LA1). Stocks of inhibitors are prepared in 100% DMSO, and added on day 0, immediately after the 1.5 hour virus absorption period. Cultures are re-fed on days 1 and 4 with medium containing the same concentration of inhibitor. Samples are harvested on day 7.

Second, chronically infected cells, containing integrated provirus and exhibiting moderate to low levels of continuous virus expression, are likely to represent in vivo reservoirs of infectious virions, which ultimately contribute to disease progression. Chronically infected cells are washed three times in growth medium and plated at density 6×10$^4$ cells per well. Inhibitors are added on day 0. Cultures are re-fed on days 1 and 3 with growth medium containing the same concentration of inhibitor. Assays are harvested on day 5.

Third, the co-cultivation assay used in these studies is a relevant model of in vivo infection since it involves cell to cell fusion and spread as well as cell free spread of HIV-1 within the culture. For this assay, 3×10$^4$ uninfected Molt4 cells are cocultivated with 3×10$^3$ H9/ LA1 or CEM/LA1 chronically infected cells per well in 24 well plates. Inhibitors are added on day 0, and the assay plates are re-fed on days 1 and 3 with growth medium containing the inhibitors. The assay is harvested on day 5. Antiviral activity is measured by several parameters: Western blot analysis of pelleted cells from treated cultures, RT levels, and p24 antigen levels in the supernatant.

The combined drug effects are calculated by the multiple drug analysis method of Chou and Talalay (Chou and Talalay, 1984, Adv. Enzyme Regul. 22:27–55) and 'Dose-Effect Analysis with Microcomputers' software (Chou and Chou, 1987, software and manual. p19–64. Elsevier Biosoft, Cambridge, UK) using the equation:

$$CI = \frac{(D)_1}{(Dx)_1} + \frac{(D)_2}{(Dx)_2} + \frac{\alpha(D)_1}{(Dx)_1} \frac{(D)_2}{(Dx)_2}$$

where CI is the combination index, $(Dx)_1$ is the dose of drug 1 required to produce x percent effect alone, $(D)_1$ is the dose of drug 1 required to produce the same x percent effect in combination with $(D)_2$. The values of $(Dx)_2$ and $(D)_2$ are similarly derived from drug 2. The value of α is determined from the plot of the dose effect curve using the median effect equation:

$$fa/fu=(D/Dm)^m$$

where fa is the fraction affected by dose D, fu is the uninfected fraction, Dm is the dose required for 50% effect and m is the slope of the dose-effect curve. For mutually exclusive drugs (i.e. similar modes of action), both drugs alone and their parallel lines in the median effect plot. Mutually nonexclusive drugs (i.E. independent mode of action) will give parallel lines in the median effect plot, but in mixture will give a concave upward curve. If the agents are mutually exclusive α is 0. and if they are mutually nonexclusive, α is 1. Values obtained assuming mutual nonexclusiveness will always be slightly greater than mutually exclusive drugs. CI values of <1 indicate synergy, values>1 indicate antagonism and values equal to 1 indicate additive effects.

The combined drug effects are also calculated by the MacSynergy computer program (Pritchard and Shipman, 1990, *Antiviral Research* 14: 181–206). This computer program allows three-dimensional graphic analysis of drug-drug interactions. The amount of synergy observed with combinations of antiviral compounds is calculated by the MacSynergy program and is represented by a three-dimensional bar graph in which the percentage of drug interaction is plotted versus drug concentrations. The amount of synergy is represented by the heights of bars in the graph and antagonism is plotted as a negative value below the floor of the graph.

6. EXAMPLE: DP-178 (SEQ ID:1) IS A POTENT INHIBITOR OF HIV-1 INFECTION

In this example, DP-178 (SEQ ID:1) is shown to be a potent inhibitor of HIV-1 mediated CD-4$^+$ cell-cell fusion and infection by cell free virus. In the fusion assay, this peptide completely blocks virus induced syncytia formation at concentrations of from 1–10 ng/ml. In the infectivity assay the inhibitory concentration is somewhat higher, blocking infection at 90 ng/ml. It is further shown that DP-178 (SEQ ID:1) shows that the antiviral activity of DP-178 (SEQ ID:1) is highly specific for HIV-1. Additionally, a synthetic peptide, DP-185 (SEQ ID:3), representing a HIV-1-derived DP-178 homolog is also found to block HIV-1-mediated syncytia formation.

6.1. Materials and Methods
6.1.1. Peptide Synthesis

Peptides were synthesized using Fast Moc chemistry on an Applied Biosystems Model 431A peptide synthesizer. Amidated peptides were prepared using Rink resin (Advanced Chemtech) while peptides containing free carboxy termini were synthesized on Wang (p-alkoxy-benzyl-alcohol) resin (Bachem). First residues were double coupled to the appropriate resin and subsequent residues were single coupled. Each coupling step was followed by acetic anhydride capping. Peptides were cleaved from the resin by treatment with trifluoracetic acid (TFA) (10 ml), H$_2$O (0.5 ml), thioanisole (0.5 ml), ethanedithiol (0.25 ml), and crystalline phenol (0.75 g). Purification was carried out by reverse phase HPLC. Approximately 50 mg samples of crude peptide were chromatographed on a Waters Delta Pak C18 column (19 mm×30 cm, 15 μ spherical) with a linear gradient; H$_2$O/acetonitrile 0.1% TFA. Lyophilized peptides were stored desiccated and peptide solutions were made in water at about 1 mg/ml. Electrospray mass spectro-metry yielded the following results: DP-178 (SEQ ID:1):4491.87 (calculated 4491.94); DP-180 (SEQ ID:2):4491.45 (calculated 4491.94); DP-185 (SEQ ID:3):not done (calculated 4546.97).

6.1.2. Virus

The HIV-1$_{LA1}$ virus was obtained from R. Gallo (Popovic, M. et al., 1984, Science 224:497–508) and propagated in CEM cells cultured in RPMI 1640 containing 10% fetal calf serum. Supernatant from the infected CEM cells was passed through a 0.2 μm filter and the infectious titer estimated in a microinfectivity assay using the AA5 cell line to support virus replication. For this purpose, 25 μl of serial diluted virus was added to 75 μl AA5 cells at a concentration of 2×10$^5$/ml in a 96-well microtitre plate. Each virus dilution was tested in triplicate. Cells were cultured for eight days by addition of fresh medium every other day. On day 8 post infection, supernatant samples were tested for virus replication as evidenced by reverse transcriptase activity released to the supernatant. The TCID$_{50}$ was calculated according to the Reed and Muench formula (Reed, L. J. et al., 1938, Am. J. Hyg. 27:493–497). The titer of the HIV-1$_{LA1}$ and HIV-1$_{MN}$ stocks used for these studies, as measured on the AA5 cell line, was approximately 1.4×10$^6$ and 3.8×10$^4$ TCID$_{50}$/ml, respectively.

6.1.3. Cell Fusion Assay

Approximately 7×10$^4$ Molt cells were incubated with 1×10$^4$CEM cells chronically infected with the HIV-1$_{LA1}$ virus in 96-well plates (one-half area cluster plates; Costar, Cambridge, Mass.) in a final volume of 100 μl culture medium as previously described (Matthews, T. J. et al., 1987, Proc. Natl. Acad. Sci. USA 84: 5424–5428). Peptide inhibitors were added in a volume of 10 μl and the cell mixtures were incubated for 24 hr. at 37° C. At that time, multinucleated giant cells were estimated by microscopic examination at a 40×magnification which allowed visualization of the entire well in a single field.

6.1.4. Cell Free Virus Infection Assay

Synthetic peptides were incubated at 37+ C. with either 247 TCID$_{50}$ (for experiment depicted in FIG. 2), or 62 TCID$_{50}$ (for experiment depicted in FIG. 3) units of HIV-1$_{LA1}$ virus or 25 TCID$_{50}$ units of HIV-2$_{NIH2}$ and CEM CD4$^+$ cells at peptide concentrations of 0, 0.04, 0.4, 4.0, and 40 μg/ml for 7 days. The resulting reverse transcriptase (RT) activity in counts per minute was determined using the assay described, below, in Section 6.1.5. See, Reed, L. J. et al., 1938, Am. J. Hyg. 27: 493–497 for an explanation of TCID$_{50}$ calculations.

6.1.5. Reverse Transcriptase Assay

The micro-reverse transcriptase (RT) assay was adapted from Goff et al. (Goff, S. et al., 1981, J. Virol. 38:239–248) and Willey et al. (Willey, R. et al., 1988, J. Virol. 62:139–147). Supernatants from virus/cell cultures are adjusted to 1% Triton-X100. A 10 μl sample of supernatant was added to 50 μl of RT cocktail in a 96-well U-bottom microtitre plate and the samples incubated at 37° C. for 90 min. The RT cocktail contained 75 mM KCl, 2 mM dithiothreitol, 5 mM MgCl$_2$, 5 μg/ml poly A (Pharmacia, cat. No. 27-4110-01), 0.25 units/ml oligo dT (Pharmacia, cat. No. 27-7858-01), 0.05% NP40, 50 mM Tris-HCl, pH 7.8, 0.5 μM non-radioactive dTTP, and 10 μCi/ml $^{32}$P-dTTP (Amersham, cat. No. PB.10167).

After the incubation period, 40 μl of reaction mixture was applied to a Schleicher and Schuell (S+S) NA45 membrane (or DE81 paper) saturated in 2xSSC buffer (0.3 M NaCl and 0.003 M sodium citrate) held in a S+S Minifold over one sheet of GB003 (S+S) filter paper, with partial vacuum applied. Each well of the minifold was washed four times with 200 μl 2×SSC, under full vacuum. The membrane was removed from the minifold and washed 2 more times in a pyrex dish with an excess of 2×SSC. Finally, the membrane was drained on absorbent paper, placed on Whatman #3 paper, covered with Saran wrap, and exposed to film overnight at −70° C.

6.2. Results

6.2.1. Peptide Inhibition of Infected Cell-Induced Syncytia Formation

The initial screen for antiviral activity assayed peptides' ability to block syncytium formation induced by overnight co-cultivation of uninfected Molt4 cells with chronically HIV-1 infected CEM cells. The results of several such experiments are presented herein. In the first of these experiments, serial DP-178 (SEQ ID:1) peptide concentrations between 10 μg/ml and 12.5 ng/ml were tested for blockade of the cell fusion process. For these experiments, CEM cells chronically infected with either HIV-$1_{LA1}$, HIV-$1_{MN}$, HIV-$1_{RF}$, or HIV-$1_{SF2}$ virus were cocultivated overnight with uninfected Molt 4 cells. The results (FIG. 4) show that DP-178 (SEQ ID:1) afforded complete protection against each of the HIV-1 isolates down to the lowest concentration of DP-178 (SEQ ID:1) used. For HIV$_{LA1}$ inhibition, the lowest concentration tested was 12.5 ng/ml; for all other HIV-1 viruses, the lowest concentration of DP-178 (SEQ ID:1) used in this study was 100 ng/ml. A second peptide, DP-180 (SEQ ID:2), containing the same amino acid residues as DP-178 (SEQ ID:1) but arranged in a random order exhibited no evidence of anti-fusogenic activity even at the high concentration of 40 μg/ml (FIG. 4). These observations indicate that the inhibitory effect of DP-178 (SEQ ID:1) is primary sequence-specific and not related to non-specific peptide/protein interactions. The actual endpoint (i.e., the lowest effective inhibitory concentration) of DP-178 inhibitory action is within the range of 1–10 ng/ml.

The next series of experiments involved the preparation and testing of a DP-178 (SEQ ID:1) homolog for its ability to inhibit HIV-1-induced syncytia formation. As shown in FIG. 1, the sequence of DP-185 (SEQ ID:3) is slightly different from DP-178 (SEQ ID:1) in that its primary sequence is taken from the HIV-$1_8$ isolate and contains several amino acid differences relative to DP-178 (SEQ ID:1) near the N terminus. As shown in FIG. 4, DP-185 (SEQ ID:3), exhibits inhibitory activity even at 312.5 ng/ml, the lowest concentration tested.

The next series of experiments involved a comparison of DP-178 (SEQ ID:1) HIV-1 and HIV-2 inhibitory activity. As shown in FIGS. 5A–5L, DP-178 (SEQ ID:1) blocked HIV-1-mediated syncytia formation at peptide concentrations below 1 ng/ml. DP-178 (SEQ ID:1) failed, however, to block HIV-2 mediated syncytia formation at concentrations as high as 10 μg/ml. This striking 4 log selectivity of DP-178 (SEQ ID:1) as an inhibitor of HIV-1-mediated cell fusion demonstrates an unexpected HIV-1 specificity in the action of DP-178 (SEQ ID:1). DP-178 (SEQ ID:1) demonstrates inhibition of HIV-1-mediated cell fusion, but the peptide's inability to inhibit HIV-2 mediated cell fusion in the same cell type at the concentrations tested provides further evidence for the high degree of selectivity associated with the antiviral action of DP-178 (SEQ ID:1).

6.2.2. Peptide inhibition of Infection by Cell-Free Virus

DP-178 (SEQ ID:1) was next tested for its ability to block CD-$4^+$ CEM cell infection by cell free HIV-1 virus. The results, shown in FIG. 2, are from an experiment in which DP-178 (SEQ ID:1) was assayed for its ability to block infection of CEM cells by an HIV-$1_{LA1}$ isolate. Included in the experiment were three control peptides, DP-116 (SEQ ID:9), DP-125 (SEQ ID:8), and DP-118 (SEQ ID:10). DP-116 (SEQ ID:9) represents a peptide previously shown to be inactive using this assay, and DP-125 (SEQ ID:8; Wild, C. et al., 1992, Proc. Natl. Acad, Sci. USA 89:10,537) and DP-118 (SEQ ID:10) are peptides which have previously been shown to be active in this assay. Each concentration (0, 0.04, 0.4, 4, and 40 μg/ml) of peptide was incubated with 247 TCID$_{50}$ units of HIV-$1_{LA1}$ virus and CEM cells. After 7 days of culture, cell-free supernatant was tested for the presence of RT activity as a measure of successful infection. The results, shown in FIG. 2, demonstrate that DP-178 (SEQ ID:1) inhibited the de novo infection process mediated by the HIV-1 viral isolate at concentrations as low as 90 ng/ml (IC50=90 ng/ml). In contrast, the two positive control peptides, DP-125 (SEQ: ID:8) and DP-118 (SEQ ID:10), had over 60-fold higher IC50 concentrations of approximately 5 μg/ml.

In a separate experiment, the HIV-1 and HIV-2 inhibitory action of DP-178 (SEQ ID:1) was tested with CEM cells and either HIV-$1_{LA1}$ or HIV-$2_{NIHZ}$. 62 TCID$_{50}$ HIV-$1_{LA1}$ or 25 GCID$_{50}$ HIV-$2_{NIHZ}$ were used in these experiments, and were incubated for 7 days. As may be seen in FIG. 3, DP-178 (SEQ ID:1) inhibited HIV-1 infection with an IC50 of about 3 ng/ml. In contrast, DP-178 (SEQ ID:1) exhibited a much higher IC50 for HIV-$2_{NIHZ}$, thus making DP-178 (SEQ ID:1) two logs more potent as a HIV-1 inhibitor than a HIV-2 inhibitor. This finding is consistent with the results of the fusion inhibition assays described, above, in Section 6.2.1, and further supports a significant level of selectivity (i.e., for HIV-1 over HIV-2).

7. EXAMPLE: THE HIV-1 INHIBITOR, DP-178 (SEQ ID:1) IS NON-CYTOTOXIC

In this Example, the 36 amino acid synthetic peptide inhibitor DP-178 (SEQ ID:1) is shown to be non-cytotoxic to cells in culture, even at the highest peptide concentrations (40 μg/ml) tested.

7.1. Materials and Methods

Cell proliferation and toxicity assay: Approximately 3.8× 10$^5$ CEM cells for each peptide concentration were incubated for 3 days at 37° C. in T25 flasks. Peptides tested were DP-178 (SEQ ID:1) and DP-116 (SEQ ID:9), as described in FIG. 1. The concentrations of each peptide used were 0, 2.5, 10, and 40 μg/ml. Cell counts were taken at incubation times of 0, 24, 48, and 72 hours.

7.2. Results

Whether the potent HIV-1 inhibitor DP-178 (SEQ ID:1) exhibited any cytotoxic effects was assessed by assaying the peptide's effects on the proliferation and viability of cells in culture. CEM cells were incubated in the presence of varying concentrations of DP-178 (SEQ ID:1), and DP-116 (SEQ ID:9), a peptide previously shown to be ineffective as a HIV inhibitor (Wild, C. et al., 1992, Proc. Natl. Acad. Sci. USA 89:10,537–10,541). Additionally, cells were incubated in the absence of either peptide.

The results of the cytoxicity study demonstrate that DP-178 (SEQ ID:1) exhibits no cytotoxic effects on cells in culture. As can be seen, below, in Table V, even the proliferation and viability characteristics of cells cultured for 3 days in the presence of the highest concentration of DP-178 (SEQ ID:1) tested (40 μg/ml) do not significantly differ from the DP-116 (SEQ ID:9) or the no-peptide controls. The cell proliferation data is also represented in graphic form in FIGS. 6A–6B. As was demonstrated in the Working Example presented above in Section 6, DP-178 (SEQ ID:1) completely inhibits HIV-1 mediated syncytia formation at peptide concentrations between 1 and 10 ng/ml, and completely inhibits cell-free viral infection at concentrations of at least 90 ng/ml. Thus, this study demonstrates that even at peptide concentrations greater than 3 log higher than the HIV inhibitory dose, DP-178 (SEQ ID:1) exhibits no cytotoxic effects.

TABLE V

| Peptide | Peptide Concentration µg/ml | % Viability at time (hours) | | | |
|---|---|---|---|---|---|
| | | 0 | 24 | 48 | 72 |
| DP178 (SEQ ID:1) | 40 | 98 | 97 | 95 | 97 |
| | 10 | 98 | 97 | 98 | 98 |
| | 2.5 | 98 | 93 | 96 | 96 |
| DP116 (SEQ ID:9) | 40 | 98 | 95 | 98 | 97 |
| | 10 | 98 | 95 | 93 | 98 |
| | 2.5 | 98 | 96 | 98 | 99 |
| No Peptide | 0 | 98 | 97 | 99 | 98 |

8. EXAMPLE: ANTI-VIRAL ACTIVITY OF DP-107 AND DP-178 PEPTIDE TRUNCATIONS AND MUTATIONS

The Example presented in this Section represents a study of the antiviral activity of DP107 and DP178 truncations and mutations. It is demonstrated that several of these DP107 and DP178 modified peptides exhibit substantial antiviral activity.

8.1. Materials and Methods

Anti-HIV assays: The antiviral assays performed were as those described, above, in Section 6.1. Assays utilized HIV-1/IIIb and/or HIV-2 NIHZ isolates. Purified peptides were used, unless otherwise noted in FIGS. 5A–5L.

Peptides: The peptides characterized in the study presented herein were:

1) FIGS. 5A–5L present peptides derived from the region around and containing the DP178 region of the HIV-1 BRU isolate. Specifically, this region spanned from gp41 amino acid residue 615 to amino acid residue 717. The peptides listed contain truncations of this region and/or mutations which vary from the DP178 sequence amino acid sequence. Further, certain of the peptides have had amino-and/or carboxy-terminal groups either added or removed, as indicated in the figures; and 2) FIGS. 6A–6B. present peptides which represent truncations of DP107 and/or the gp41 region surrounding the DP107 amino acid sequence of HIV-1 BRU isolate. Certain of the peptides are unblocked or biotinylated, as indicated in the figures.

Blocked peptides contained an acyl N-terminus and an amido C-terminus.

8.2. Results

Anti-HIV antiviral data was obtained with the group 1 DP178-derived peptides listed in FIGS. 5A–5L. The full-length, non-mutant DP178 peptide (referred to in FIGS. 5A–5L as T20) results shown are for 4 ng/ml.

In FIGS. 5A–5L, a number of the DP178 truncations exhibited a high level of antiviral activity, as evidenced by their low $IC_{50}$ values. These include, for example, test peptides T-50, T-624, T-636 to T-641, T-645 to T-650, T-652 to T-654 and T-656. T-50 represents a test peptide which contains a point mutation, as indicated by the residue's shaded background. The HIV-1-derived test peptides exhibited a distinct strain-specific antiviral activity, in that none of the peptides tested on the HIV-2 NIHZ isolate demonstrated appreciable anti-HIV-2 antiviral activity.

Among the peptides listed in FIGS. 5E–5H, are test peptides representing the amino (T-4) and carboxy (T-3) terminal halves of DP178 that were tested. The amino terminal peptide was not active ($IC_{50}$>400 µg/ml) whereas the carboxy terminal peptide showed potent antiviral activity ($IC_{50}$=3 µg/ml). A number of additional test peptides also exhibited a high level of antiviral activity. These included, for example, T-61/T-102, T-217 to T-221, T-235, T-381, T-677, T-377, T-590, T-378, T-591, T-271 to T-272, T-611, T-222 to T-223 and T-60/T-224. Certain of the antiviral peptides contain point mutations and/or amino acid residue additions which vary from the DP178 amino acid sequence.

In FIGS. 5I–5L, point mutations and/or amino and/or carboxy-terminal modifications are introduced into the DP178 amino acid sequence itself. As shown in the figures, the majority of the test peptides listed exhibit potent antiviral activity.

Truncations of the DP107 peptide (also referred to as T21) were also produced and tested, as shown in FIGS. 6A–6B. FIGS. 6A–6B also present data concerning blocked and unblocked peptides which contain additional amino acid residues from the gp41 region in which the DP107 sequence resides. Most of these peptides showed antiviral activity, as evidenced by their low $IC_{50}$ values.

Thus, the results presented in this Section demonstrate that not only do the full length DP-107 and DP-178 peptides exhibit potent antiviral activity, but truncations of these peptides also possess substantial antiviral character.

9. EXAMPLE: POTENTIAL SIV DP178/DP107 ANALOGS: ANTIVIRL CHARACTERIZATION

In the Example presented herein, simian immunodeficiency virus (SIV) DP178-like peptides identified by utilizing the computer-assisted search motifs described above, were tested for anti-SIV activity. It is demonstrated that several of the identified peptides exhibit potent antiviral capability.

9.1. Materials and Methods

Anti-SIV antiviral assays: The assay utilized herein were as reported in Langolis et al. (Langolis, A. J. et al., 1991, AIDS Research and Human Retroviruses 7:713–720).

Peptides: The peptides characterized in the study presented herein were peptides T-391 to T-400, as shown in FIGS. 7A–7B. These peptides represent a walk through the DP178-like region of the SIV TM protein.

Each peptide was tested at 2-fold serial dilutions ranging from 100 µg/ml to approximately 100 ng/ml. For each of the assays, a well containing no peptide was also used.

9.2. Results

The data summarized in FIGS. 7A–7B represent antiviral information obtained via "peptide walks" through the DP178-like region of the SIV TM protein.

As shown in FIGS. 7A–7B, peptides T-391 to T-400 were tested and exhibited a potent antiviral activity as crude peptides.

Thus, the computer assisted searches described, hereinabove, as in for example, the Example presented in Section 8, for example, successfully identified viral peptide domains that represent highly promising anti-SIV antiviral compounds.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of treating HIV-1 infection in a subject, comprising administering to the subject a therapeutically effective amount of DP-178 having SEQ ID NO:1, or a pharmaceutically acceptable derivative thereof, and a therapeutically effective amount of at least one other therapeutic agent which is a reverse transcriptase inhibitor or an inhibitor of HIV-1 protease.

2. The method of claim 1, wherein the therapeutic agent is a reverse transcriptase inhibitor.

3. The method of claim 2, wherein the reverse transcriptase inhibitor is AZT, ddI, ddC, ddA, d4T or 3TC.

4. The method of claim 1, wherein said DP-178 derivative is a peptide selected from the group consisting of:

T-624 having SEQ ID NO:55;
T-636 having SEQ ID NO:56;

T-637 having SEQ ID NO:57;
T-638 having SEQ ID NO:58;
T-639 having SEQ ID NO:59;
T-640 having SEQ ID NO:60;
T-641 having SEQ ID NO:61;
T-645 having SEQ ID NO:62;
T-646 having SEQ ID NO:63;
T-647 having SEQ ID NO:64;
T-648 having SEQ ID NO:65;
T-649 having SEQ ID NO:66;
T-650 having SEQ ID NO:67;
T-652 having SEQ ID NO:68;
T-653 having SEQ ID NO:69;
T-654 having SEQ ID NO:70; and
T-656 having SEQ ID NO:71.

5. The method of claim 1, wherein said administration is sequential.

6. The method of claim 1, wherein said administration is simultaneous.

7. The method of claim 1, wherein said administration of at least one therapeutic agent is oral.

8. The method of claim 1, wherein said administration is parenteral.

9. The method of claim 8, wherein said parenteral administration is intravenous.

10. The method of claim 1, wherein the therapeutic agent is an inhibitor of HIV-1 protease.

11. The method of claim 10, wherein the inhibitor of HIV-1 protease is indinavir.

12. The method of claim 2, wherein the reverse transcriptase inhibitor is AZT.

13. The method of claim 2, wherein the reverse transcriptase inhibitor is 3TC.

14. A method of inhibiting HIV-1 replication in a subject, comprising administering to the subject a therapeutically effective amount of DP-178 having SEQ ID NO:1, or a pharmaceutically acceptable derivative thereof, and a therapeutically effective amount of at least one other therapeutic agent which is a reverse transcriptase inhibitor or an inhibitor of HIV-1 protease.

15. The method of claim 14, wherein the therapeutic agent is a reverse transcriptase inhibitor.

16. The method of claim 15, wherein the reverse transcriptase inhibitor is AZT, ddI, ddC, ddA, d4T or 3TC.

17. The method of claim 14, wherein said administration is sequential.

18. The method of claim 14, wherein said administration is simultaneous.

19. The method of claim 14, wherein said administration of at least one therapeutic agent is oral.

20. The method of claim 14, wherein said administration is parenteral.

21. The method of claim 20, wherein said administration is intravenous.

22. The method of claim 14, wherein the therapeutic agent is an inhibitor of HIV-1 protease.

23. The method of claim 22, wherein the inhibitor of HIV-1 protease is indinavir.

24. The method of claim 15, wherein the reverse transcriptase inhibitor is AZT.

25. The method of claim 15, wherein the reverse transcriptase inhibitor is 3TC.

26. A pharmaceutical composition useful for the treatment of HIV-1 infection, comprising a therapeutically effective amount of DP-178 having SEQ ID NO:1, or a pharmaceutically acceptable derivative thereof, a therapeutically effective amount of at least one other therapeutic agent which is a reverse transcriptase inhibitor or an inhibitor of HIV-1 protease, and a pharmaceutically acceptable carrier.

27. The pharmaceutical composition of claim 26, wherein the therapeutic agent is a reverse transcriptase inhibitor.

28. The pharmaceutical composition of claim 27 wherein the reverse transcriptase inhibitor is AZT, ddI, ddC, ddA, d4T or 3TC.

29. The pharmaceutical composition of claim 26, wherein the therapeutic agent is an inhibitor of HIV-1 protease.

30. The pharmaceutical composition of claim 29, wherein the inhibitor of HIV-1 protease is indinavir.

31. The pharmaceutical composition of claim 27, wherein the reverse transcriptase inhibitor is AZT.

32. The pharmaceutical composition of claim 27, wherein the reverse transcriptase inhibitor is 3TC.

* * * * *